US006436399B1

(12) United States Patent
Rikihisa et al.

(10) Patent No.: US 6,436,399 B1
(45) Date of Patent: Aug. 20, 2002

(54) NUCLEIC ACID ENCODING THE MAJOR OUTER MEMBRANE PROTEIN OF THE CAUSATIVE AGENT OF HUMAN GRANULOCYTIC EHRLICHIOSIS AND PEPTIDES ENCODED THEREBY

(75) Inventors: Yasuko Rikihisa, Worthington; Ning Zhi; Norio Ohashi, both of Columbus, all of OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/288,339

(22) Filed: Apr. 8, 1999

Related U.S. Application Data
(60) Provisional application No. 60/081,192, filed on Apr. 9, 1998.

(51) Int. Cl.$^7$ ...................... A61K 39/395; A61K 39/40; A61K 39/38; A61K 39/02; C12N 1/00

(52) U.S. Cl. ................................ 424/139.1; 424/164.1; 424/184.1; 424/185.1; 424/190.1; 435/243; 530/300; 530/350; 536/23.7

(58) Field of Search ........................... 424/139.1, 164.1, 424/184.1, 185.1, 190.1; 435/243; 530/300, 350; 536/23.7

(56) References Cited

U.S. PATENT DOCUMENTS 6,207,169 B1    3/2001    Reed et al. ............... 424/234.1
6,231,869 B1    5/2001    Reed et al. ............... 424/234.1

OTHER PUBLICATIONS

GenBank Accession L01987, Dec. 3, 1998.
GenBank Accession AF029322, Aug. 13, 1998.
GenBank Accession AF029323, Aug. 13, 1998.
GenBank Accession AF059181, Jul. 5, 1998.
GenBank Accession U07862, Jan. 5, 1995.
GenBank Accession AF107766, Mar. 18, 1999.
GenBank Accession AF107767, Mar. 18, 1999.
GenBank Accession AF135254, Jun. 30, 1999.
GenBank Accession AF135255, Jun. 30, 1999.
GenBank Accession AF135256, Jun. 30, 1999.
GenBank Accession AF135257, Jun. 30, 1999.
GenBank Accession AF135258, Jun. 30, 1999.
GenBank Accession AF135259, Jun. 30, 1999.
GenBank Accession AF135260, Jun. 30, 1999.
GenBank Accession AF135261, Jun. 30, 1999.
GenBank Accession AF135262, Jun. 30, 1999.
GenBank Accession AF135263, Jun. 30, 1999.
GenBank Accession U36193, Aug. 8, 1996.
GenBank Accession AF037599, Jul. 17, 1998.
"Multiple p44 Genes Encoding Major Outer Membrane Proteins Are Expressed in Human Granulycytic Ehrlichiosis Agent" by Zhi, et al., *The Journal of Biological Chemistry*, vol. 274, No. 25, Jun. 18, 1999, pp. 17828–17863.

"Cloning and Expression of the 44–Kilodalton Major Outer Membrane Protein Agent of the Human Granulocytic Ehrlichiosis Agent and Application of the Recombinant Protein to Serodiagnosis" by Zhi, et al., *Journal of Clinical Microbiology*, vol. 36, No. 6, Jun. 1998, pp. 1666–1673.
"Major Antigenic Proteins of the Agent of Human Granulocytic Ehrlichiosis Are Encoded by Members of a Multigene Family" by Murphy, et al., *Infection and Immunity*, vol. 66, No. 8, Aug. 1998, pp. 3711–3718.
"Cloning of the Gene Encoding the 44–Kilodalton Antigen of the Agent Human Granulocytic Ehrlichiosis and Characterization of the Humoral Response" by Ijdo, et al., *Infection and Immunity*, vol. 66, No. 7, Jul. 1998, pp. 3264–3269.
"Ultrastructural and Antigenic Characterization of a Granulocytic Ehrlichiosis Agent Directly Isolated and Stably Cultivated from a Patient in New York State" by Rikihisa, et al., *The Journal of Infectious Diseases*, 1997:175:210–213.
"Comparison of Major Antigenic Proteins of Six Strains of the Human Granulocytic Ehrlichiosis Agent by Western Immunoblot Analysis" by Zhi, et al., *Journal of Clinical Microbiology*, vol. 35, No. 10, Oct. 1887, pp. 2606–2611.
"Cloning and Characterization of Multigenes Encoding the Immunodominant 30–Kilodalton Major Outer Membrane Proteins of *Ehrlichia canis* and Application of the Recombinant Protein for Serodiagnosis" By Ohashi, et al., *Journal of Clinical Microbiology*, vol. 36, No. 9, Sep. 1998, pp. 2671–2680.
"Characterization of Monoclonal Antibodies to the 44–Kilodalton Major Outer Membrane Protein of the Human Granulocytic Ehrlichiosis Agent" by Kim, et al., *Journal of Clinical Microbiology*, vol. 36, No. 11, Nov. 1998, pp. 3278–3284.

*Primary Examiner*—Rodney P Swartz
(74) *Attorney, Agent, or Firm*—Calfee, Halter & Griswold LLP

(57) ABSTRACT

The present invention relates to diagnostic tools for serodiagnosing HGE. The diagnostic tools are structurally related proteins, the "Group 44 proteins", and to antibodies to such proteins. the Group 44 proteins comprise a single central hypervariable region of approximately 94 amino acid residues, a first conserved region and a second conserved region which flank the central hypervariable region. The hypervariable region of each Group 44 protein has a higher hydrophilicity, a higher antigenic index, and a higher surface probability than either the first conserved region or the second conserved region of the respective protein. The hypervariable region is basic and has an isoelectric point, i.e., a pI, of from about 7.1 to about 9.2 and a molecular mass, i.e., an Mr, of from about 8.5 kDa to about 11 kDa. The Group 44 proteins comprise the P44 protein, the P44-2 protein, the P44-12 protein, the P44-15 protein, the P44-18 protein, and the P44-19 protein and variants of such proteins. The present invention also provides isolated polynucleotides or nucleic acids, referred to collectively hereinafter as the "Group 44 polynucleotides", which encode the Group 44 proteins and fragments thereof. The present invention provides synthetic oligopeptides of 14–16 amino acids in length. Each of the oligopeptides comprise a sequence which is specific to one Group 44 protein. The present invention also relates to antibodies which are immunospecific for and bind to members of the P44 family of proteinss. The present invention also relates to kits containing reagents for diagnosing HGE.

11 Claims, 12 Drawing Sheets

```
FEATURES             Location/Qualifiers
     source          1..1278
                     /organism="Ehrlichia sp. 'HGE agent'"
                     /strain="HZ(Isolate 13)"
                     /db_xref="taxon:59888"
     gene            1..1278
                     /note="member of p44 multigene family"
                     /gene="p44-2"
     CDS             1..1278
                     /gene="p44-2"
                     /note="major outer membrane protein"
                     /codon_start=1
                     /product="P44-2"
                     /translation="MMSMAIVMAGNDVRAHDDVSALENGGAGYFYV
                     GLDYSPAFSKIRDFSIRESNGETKAVYPYLKDGKSVKLESHKFDWN
                     TPDPRIGFKDNMLVAMEGSVGYGIGGARVELEIGYERFKTKGIRDS
                     GSKEDEADTVYLLAKELAYDVVTGQTDKLTAALAKTSGKDIVQFAN
                     AVKISSSAIDGKVCTGSHADLAPGTNAGKKFVVNPEASGSTDGDTS
                     QCSGLGHSSGVTQNPKLFSTFVDTVKIAEDKNWPTGRAKSNTSLKT
                     GDTNSNAKAVATDLVQELTPEEKTIVAGLLAKTIEGGEVVEIRAVS
                     STSVMVNACYDLLSEGLCVVPYACVGLGGNFVGVVDGHITPKLAYR
                     LKAGLSYQLSPVISAFAGGFYHRVVGDVYDDLPAQRLVDDTSPAG
                     RTKDTAIANFSMAYVGGEFGVRFAF"
BASE COUNT      323 a    215 c    370 g    370 t
ORIGIN
   1 atgatgtcaa tggctatagt catggctggg aatgatgtca gggctcatga tgacgttagc
  61 gctttggaga atggtggtgc gggatatttc tatgttggtt tggattacag tccagcgttt
 121 agcaagataa gagattttag tataagggag agtaacggag agacaaaggc agtatatcca
 181 tacttaaagg atggaaagag tgtaaagctt gagtcgcaca gtttgactg gaacacacct
 241 gatcctcgga ttgggtttaa ggacaacatg cttgtagcta tggaaggcag tgttggttat
 301 ggtattggtg gtgccagggt tgagcttgag attggttacg agcgcttcaa gaccaagggt
 361 attagagata gtggtagtaa ggaagatgaa gctgatacag tatatctact agctaaggag
 421 ttagcttatg atgttgttac tggacagact gataagctta ccgctgctct tgccaagacc
 481 tccggtaaag atatcgttca gtttgcgaat gctgtgaaaa tttctagctc tgccatcgat
 541 gggaaggttt gtactggtag ccatgctgac ctagcgcctg gtacgaatgc ggggaaaaag
 601 ttcgttgtga acccggaagc cagcgggagt actgatgggg atacgtcaca gtgtagtggt
 661 ttagggcata gtagtggtgt tacacagaat ccgaagttat ttagtacttt tgtggacact
 721 gtgaagattg ctgaggataa aaactggccg acgggcaggg caaaatcgaa cacatcactg
 781 aagacgggtg atactaatag taacgccaaa gccgtggcta cagacctagt acaggagcta
 841 acccctgaag aaaaaaccat agtagcaggg ttactagcta agactattga aggggggtgaa
 901 gttgttgaga tcagggcggt ttcttctact tccgtaatgg tcaatgcttg ttatgatctt
 961 cttagtgaag gtttatgtgt tgttccttat gcttgtgttg gtcttggcgg taacttcgtg
1021 ggcgtggttg atggccatat cactcctaag cttgcttata gattaaaggc tgggttgagt
1081 tatcagctct ctcctgtaat ctccgctttt gcgggtggat ctaccatcg cgttgtggga
1141 gatggcgttt atgatgatct gccggctcaa cgtcttgtag atgatactag tccggcgggc
1201 cgtactaagg atactgctat tgctaacttc tccatggctt atgtcggtgg ggaatttggt
1261 gttaggttcg ctttttaa
```

Fig. 3

```
FEATURES             Location/Qualifiers
     source          1..1176
                     /organism="Ehrlichia sp. 'HGE agent'"
                     /strain="HZ(Isolate 13)"
                     /db_xref="taxon:59888"
     gene            1..1176
                     /note="member of p44 multigene family"
                     /gene="p44-12"
     CDS             1..1176
                     /gene="p44-12"
                     /note="major outer membrane protein"
                     /codon_start=1
                     /product="P44-2"
                     /translation="MMSMAIVMAGNDVRAHDDVSALETGGAGYFYV
                     GLDYSPAFSKIRDFSIRESNGETKAVYPYLKDGKSVKLESHKFDWN
                     TPDPRIGFKDNMLVAMEGSVGYGIGGARVELEIGYERFKTKGIRDS
                     GSKEDEADTVYLLAKELAYDVVTGQTDNLAAALAKTSGKDIVQFAK
                     AVGVSHPGIDKKVCDGGHARGKKSGDNGSLADYTDGGASQTNKTAQ
                     CSGMGTGKAGKRGLGLTEFVNKTKVGEGKNWPTGYVNDGDNVNVLG
                     DTNGNAEAVAKDLVQELTPEEKTIVAGLLAKTIEGGEVVEIRAVSS
                     TSVMVNACYDLLSEGLGVVPYACVGLGGNFVGVVDGHITPKLAYRL
                     KAGLSYQLSPVISAFAGGFYHRVVGDGVYDDLPAQLP"
BASE COUNT       301 a    191 c    354 g    330 t
ORIGIN
   1  atgatgtcta tggctatagt catggctggg aatgatgtca gggctcatga tgacgttagc
  61  gctttggaga ctggtggtgc gggatatttc tatgttggct tggattacag tccagcgttt
 121  agcaagataa gagattttag tataagggag agtaacggag agactaaggc agtatatcca
 181  tacttaaagg atggaaagag tgtaaagcta gagtcacaca agtttgactg gaacactcct
 241  gatcctcgga ttgggtttaa ggacaacatg cttgtagcta tggaaggcag tgttggttat
 301  ggtattggtg gtgccagggt tgagcttgag attggttacg agcgcttcaa gaccaagggt
 361  attagagata gtggtagtaa ggaagatgaa gctgatacag tatatctact agctaaggag
 421  ttagcttatg atgttgttac tggcagact gataaccttg ctgctgctct tgccaagacc
 481  tctggtaaag atattgttca gtttgctaag gcggttgggg tttctcatcc cggtattgat
 541  aagaaggttt gtgatggggg tcatgcacgg ggaaaaaaga gtggagataa tggctcgctg
 601  gccgactata cggatggtgg cgcgtcacag acgaataaga cggctcagtg tagtggtatg
 661  ggaaccggca aagccggcaa gagaggattg gcttgactg agtttgttaa caaaacaaag
 721  gttggagaag gtaagaattg gccaacgggg tacgttaatg atggcgacaa cgttaatgtg
 781  ctcggcgata cgaatggtaa cgccgaagcc gtagctaaag acctagtaca ggagctaacc
 841  cctgaagaaa aaaccatagt agcaggggtta ctagctaaga ctattgaagg gggtgaagtt
 901  gttgagatca gggcggtttc ttctacttcc gtaatggtca atgcttgtta tgatcttctt
 961  agtgaaggtt taggtgttgt tccttatgct tgtgttggtc ttggcggtaa cttcgtgggc
1021  gtggttgatg gccatatcac tcctaagctt gcttatagat aaaggctgg gttgagttat
1081  cagctctctc ctgtaatctc cgcttttgcg ggtggattct accatcgcgt tgtgggagat
1141  ggcgtttatg atgatctgcc ggctcaacta ccttga
```

Fig. 4

| FEATURES | Location/Qualifiers |
|---|---|
| source | 1..837 |
| | /organism="Ehrlichia sp. 'HGE agent'" |
| | /strain="HZ(Isolate 13)" |
| | /db_xref="taxon:59888" |
| gene | <1..837 |
| | /note="member of p44 multigene family" |
| | /gene="p44-15" |
| CDS | <1..837 |
| | /gene="p44-15" |
| | /note="major outer membrane protein" |
| | /codon_start=1 |
| | /product="P44-15" |
| | /translation="FTLEPLSGRRNRNIKSLISLLLRPRVLEISGS |
| | KEDEADTVYLLAKELAYDVVTGQTDNLAAALAKTSGKDFVQFAKAV |
| | GVSHPSIDGKVCKTKADSSKKFPLYSDETHTKGASEGRTSLCGDNG |
| | SSTITNSGANVSETGQVFRDFIRATLKEDGSKNWPTSSGTGTPKPV |
| | TNDNAKAVAKDLVQELTPEEKTIVAGLLAKTIEGGEVIEIRAVSST |
| | SVMVNACYDLLSEGLGVVPYACVGLVGNFVGVVDGHITPKLAYRLK |
| | AGLSYQLSPVISSFSV" |
| BASE COUNT | 236 a   140 c   222 g   239 t |
| ORIGIN | |

```
  1 tttaccttgg aaccattatc agggagaaga aataggaata ttaagagtct aataagttta
 61 ttattgagac caagggtatt agagattagt ggtagtaagg aagatgaagc tgatacagta
121 tatctactag ctaaggagtt agcttatgat gttgttactg ggcagactga taaccttgcc
181 gctgctctgg ccaaaacctc cggtaaagac tttgtccagt ttgctaaggc ggttggggtt
241 tctcatccta gtattgatgg gaaggtttgt aagacgaagg cggatagctc gaagaaattt
301 ccgttatata gtgacgaaac gcacacgaag ggggcaagtg aggggagaac gtctttgtgc
361 ggtgacaatg gtagttctac gataacaaac agtggtgcga atgtaagtga aactgggcag
421 gttttagga ttttatcag ggcaacgctg aagaggatg gtagtaaaaa ctggccaact
481 tcaagcggca cgggaactcc aaaacctgtc acgaacgaca acgccaaagc cgtagctaaa
541 gacctagtac aggagctaac ccctgaagaa aaaccatag tagcagggtt actagctaaa
601 actattgaag gtggtgaggt tattgaaatc agggcggttt cttctacttc tgtgatggtc
661 aatgcttgtt atgatcttct tagtgaaggt ttaggtgttg tcccttatgc ttgtgttggt
721 cttgtgggta acttcgtagg tgttgttgat gggcatatca ctcctaagct tgcttataga
781 ttaaaggctg gcttgagtta tcagctctct cctgtaatct cttctttctc agtatga
```

Fig. 5

```
FEATURES             Location/Qualifiers
     source          1..759
                     /organism="Ehrlichia sp. 'HGE agent'"
                     /strain="HZ(Isolate 13)"
                     /db_xref="taxon:59888"
     gene            <1..759
                     /note="member of p44 multigene family"
                     /gene="p44-18"
     CDS             <1..759
                     /gene="p44-18"
                     /note="major outer membrane protein"
                     /codon_start=1
                     /product="P44-18"
                     /translation="SAGAYAIILIIENKTKGIRDSGSKEDEADTVY
                     LLAKELAYDVVTGQTDNLAAALAKTSGKDIVQFAKAVEISNSGIGK
                     KVCETKRKDGDTTNRFAKYIVGAGDSSNAGTSLCGGKNQKSSDTDT
                     GVEKAQALHDFVSNTLSDGTKNWPTSSETSKSNNDNAKAVAGDLTK
                     KLTPEEKTIVAGLLAKTIEGGEVVEIRAVSSTSVMVNACYDLLSEG
                     LGVVPYACVGLGGNFVGVVDEYSTIRPSLTLYARRK"
BASE COUNT      213 a    129 c    204 g    213 t
ORIGIN
  1 tctgccggag cctatgcaat aattcttatt attgaaaaca agaccaaggg tattagagat
 61 agtggtagta aggaagatga agctgataca gtatatctac tagctaagga gttagcttat
121 gatgttgtta ctgggcagac tgataacctt gccgctgctc ttgccaaaac ctcaggtaag
181 gacatcgttc agtttgctaa ggccgtggag atttctaatt ccggtattgg taagaaggtg
241 tgtgagacaa agcggaagga tggtgatact acgaacaggt ttgcaaagta tatagttggt
301 gcgggtgata gtagcaatgc tggtacatca ttgtgtggtg gtaagaacca aaagagttcg
361 gacacagaca ccggggtgga gaaggctcag gctctgcatg actttgtttc taacacattg
421 agtgatggta ctaagaactg gcctacgtcg agtgaaacgt ctaaatcgaa taacgacaac
481 gccaaagctg tagcgggaga cttaactaag aagctcaccc ctgaagaaaa aaccatagta
541 gcagggttac tagctaagac tattgaaggt ggtgaggttg ttgaaattag ggcggtttct
601 tctacttctg tgatggttaa tgcttgttat gatcttctta gtgaaggttt aggcgttgtt
661 ccttatgctt gtgttggtct cggtggaaac ttcgttggtg ttgttgacga gtacagcaca
721 atccgtccgt ctttaaccct atatgcccgt agaaagtaa
```

Fig. 6

```
FEATURES             Location/Qualifiers
     source          1..492
                     /organism="Ehrlichia sp. 'HGE agent'"
                     /strain="HZ(Isoalte 13)"
                     /db_xref="taxon:59888"
     gene            <1..>492
                     /note="member of p44 multigene family"
                     /gene="p44-19"
     CDS             <1..>492
                     /gene="p44-19"
                     /note="major outer membrane protein"
                     /codon_start=1
                     /product="P44-19"
                     /translation="AKELAYDVVTGQTDNLAAALAKTSGKDIVQFA
                     KAVEISSPTIDGKICKINTGSNKYGTGTNSGELTCGVGHASGSLGA
                     ANGAFKDFRQHVLEVESHKHWPTTQGSSDKGSNNATKVAGELTKLT
                     TEEKTIVAGLLAKTIEGGEVVEIRAVSSTSVMVNACYDLL"
BASE COUNT        149 a      90 c     126 g      127 t
ORIGIN
  1  gctaaggagt tagcttatga tgttgttact ggacagactg ataaccttgc tgctgctctt
 61  gccaaaacct caggtaagga catcgttcag tttgctaagg cggtggagat atcctccccc
121  accattgatg ggaagatttg taagataaat acaggaagta ataaatacgg cactggaaca
181  aattctggag aactcacttg tggagttggc cacgcgagcg gatctctagg agcggcgaac
241  ggagccttta aggattttcg acagcatgtg ttagaagttg aaagtcataa acattggcct
301  actacgcagg gttctagtga taaaggtagt aataacgcaa caaaggtagc cggagaacta
361  acaaagctca ccacagaaga aaaaaccata gtagcagggt tactagctaa aactattgaa
421  gggggagagg ttgttgaaat cagggctgtc tcttctactt ctgtgatggt taatgcttgt
481  tatgatcttc tt
```

Fig. 10

NUCLEIC ACID ENCODING THE MAJOR OUTER MEMBRANE PROTEIN OF THE CAUSATIVE AGENT OF HUMAN GRANULOCYTIC EHRLICHIOSIS AND PEPTIDES ENCODED THEREBY

This application claims the benefit of U.S. Provisional No. 60/081,192, filed Apr. 9, 1998.

BACKGROUND

This work was supported by grant RO1 AI33123 and grant RO1 A140934 from the National Institutes of Health. The Government has certain rights in this invention.

Human granulocytic ehrlichiosis (HGE), an emerging human infectious disease, is increasingly being recognized in the United States. Serological and PCR studies suggest that HGE infection also exists in Europe. HGE is caused by infection with an obligatory intracellular bacterium, HGE agent. Comparison of 16S rRNA gene sequences and ultrastructure indicates that the HGE agent is closely related to *Ehrlichia phagocytophila*, the agent of tick-borne fever, and *E. equi*, the agent of equine ehrlichiosis. The HGE agent is transmitted by the Ixodes sp. tick, and the white-footed mouse is considered to be the major reservoir of the HGE agent in the United States.

HGE infection is characterized by the presence of ehrlichial inclusions called morulae in human or animal peripheral blood granulocytes. The symptoms of HGE include chills, headache, myalgia, hematological abnormalities, including leukopenia and thrombocytopenia. HGE frequently requires prolonged hospitalization. When treatment is delayed due to misdiagnosis, HGE can be fatal.

Although several laboratories have used IFA testing, acute-phase blood smear, nested PCR, and culture isolation for diagnosis of HGE, each of these diagnostic tests has disadvantages. IFA testing using the HGE agent or *E. equi*-infected cells has been most widely used for serodiagnosis of ehrlichiosis. IFA requires a tissue culture system for preparation of HGE-infected cell antigen slides, fluorescent microscope, and trained persons especially for evaluation of the serum reactivity to the antigen on the slide. The nested PCR, while better suited to early diagnosis of HGE than IFA testing, requires thermocycler and trained personel, and the reagents are relatively expensive. The sensitivity of culture isolation in HGE diagnosis seems to be relatively lower than that of IFA test and the nested PCR. Moreover, diagnosis by culture isolation requires serologic evidence, PCR, or 16S rRNA gene sequence for confirmation of the identity of new isolates.

Accordingly, a convenient and sensitive method with high specificity for the diagnosis of HGE infection is still desirable.

SUMMARY OF THE INVENTION

The present invention relates to improved diagnostic tools for serodiagnosing HGE. diagnostic tools are structurally related proteins, collectively referred to hereinafter as the "Group 44 proteins", and to antibodies to such proteins. As compared to each other, the Group 44 proteins comprise a single central hypervariable region of approximately 94 amino acid residues, a first conserved region and a second conserved region which flank the central hypervariable region. The first conserved region comprises 52 amino acids and is linked directly or through a linker of from 1 to 10 amino acids to the amino terminus, i.e., the N-terminus, of the hypervariable region. The second conserved region comprises about 56 amino acids and is linked either directly or through a linker of from 1 to 10 amino acids to the carboxy terminus, i.e., the C-terminus, of the hypervariable region. The hypervariable region of each Group 44 protein has a higher hydrophilicity, a higher antigenic index, and a higher surface probability than either the first conserved region or the second conserved region of the respective protein. The hypervariable region is basic and has an isoelectric point, i.e., a pI, of from about 7.1 to about 9.2 and a molecular mass, i.e., an Mr, of from about 8.5 kDa to about 11 kDa. The hypervariable region has a first semiconserved region of 8 amino acids near the amino terminus thereof and a second semiconserved region of 11 amino acids at the carboxy terminus thereof. The hypervariable region also contains a third semiconserved region of 6 amino acids. It is believed that the third semiconserved region, which is between and separated from the first semiconserved region and the second semiconserved region is perhaps involved in adhesion of the HGE agent to other cells.

The Group 44 proteins comprise the P44 protein, the P44-2 protein, the P44-12 protein, the P44-15 protein, the P44-18 protein, and the P44-19 protein and variants of such proteins. The P44 protein and variants thereof specifically bind to antibodies found in the sera from horses infected with the HGE agent and to antibodies in the sera from humans infected with the HGE agent and horse anti-*Ehrlichia equi* serum. The P44 protein and variants thereof do not bind to antibodies in sera from patients infected with *E.chaffeensis* or *Borrelia burgdorferi*. In one embodiment, the P44 protein comprises the amino acid sequence, SEQ ID NO: 2, shown in FIG. 1.

The P44-2 protein has a molecular mass of about 45 kDa. In one embodiment the P44-2 protein comprises the amino acid sequence, SEQ ID NO: 4, shown in FIG. 2.

The P44-12 protein has a molecular mass of about 41.2 kDa. In one embodiment the P44-12 protein comprises the amino acid sequence, SEQ ID NO: 6, shown in FIG. 3. The P44-15 protein comprises a hypervariable region which encodes a polypeptide having a molecular mass of about 10.8 kDa. In one embodiment, the P44-15 protein comprises the amino acid sequence, SEQ ID NO: 8, shown in FIG. 4. The P44-18 protein comprises a hypervariable region which encodes a polypeptide having a molecular mass of about 26.4 kDa. In one embodiment, the P44-18 protein comprises the amino acid sequence, SEQ ID NO:10 shown in FIG. 5. The P44-19 protein comprises a hypervariable region which encodes a polypeptide having a molecular mass of about 8.6 kDa and an isoelectric point of about 8.8. The P44-19 protein comprises th[0085] amino acid sequence, SEQ ID NO: 12, shown in FIG. 6.

The Group 44 proteins are immunogenic and, thus, are useful for preparing antibodies. The isolated proteins of the P44 family, either individually or as a panel of proteins, are useful for detecting antibodies to the HGE agent in the blood of patients with clinical signs of HGE. The isolated, individual Group 44 proteins are also useful in an immunogenic composition for ameliorating HGE. The isolated, individual Group 44 proteins are also useful in a vaccine for protecting against infection with the HGE agent.

The present invention also provides isolated polynucleotides or nucleic acids, referred to collectively hereinafter as the "Group 44 polynucleotides", which encode the Group 44 proteins and fragments thereof. The P44 polynucleotides encode the P44 protein. One embodiment of the P44 polynucleotides comprises the nucleotide sequence, SEQ ID NO:1, shown in FIG. 1. The P44-2 polynucleotides encode the P44-2 protein. One embodiment of the P44-2 polynucleotides comprises the nucleotide sequence, SEQ ID NO: 3, shown in FIG. 2. The P44-12 polynucleotides encode the P44-12. One embodiment of the P44-12 polynucleotides comprises the nucleotide sequence, SEQ ID NO: 5, shown in FIG. 3. The P44-15 polynucleotides encode the P44-15 protein. One embodiment of the P44-15 polynucleotides comprises the nucleotide sequence, SEQ ID NO: 7, shown in FIG. 4. The P44-18 polynucleotides encode the P44-18 protein. One embodiment of the P44-18 polynucleotides comprises the nucleotide sequence, SEQ ID NO: 9, shown in FIG. 5. The P44-19 polynucleotides encode the P 44-19 protein. One embodiment of the P44-19 polynucleotides comprises the nucleotide sequence, SEQ ID NO: 11, shown in FIG. 6. The Group 44 polynucleotides are useful for preparing the Group 44 proteins and variants thereof. Group 44 polynucleotides which encode fragments of the Group 44 proteins are useful as primers and probes.

The present invention provides synthetic oligopeptides of 14-16 amino acids in length. Each of the oligopeptides comprise a sequence which is specific to one Group 44 protein. Such peptides are useful for preparing antibodies which are immunospecific for one or more Group 44 proteins.

The present invention also relates to antibodies which are immunospecific for and bind to members of the P44 family of proteins. Such antibodies are useful for immunolabeling isolates of the HGE agent and for detecting the presence of HGE in body fluids, tissues, and particularly, monocytes and macrophages. The present invention also relates to kits containing reagents for diagnosing HGE.

BRIEF DESCRIPTION OF THE FIGURES

Figure 1:
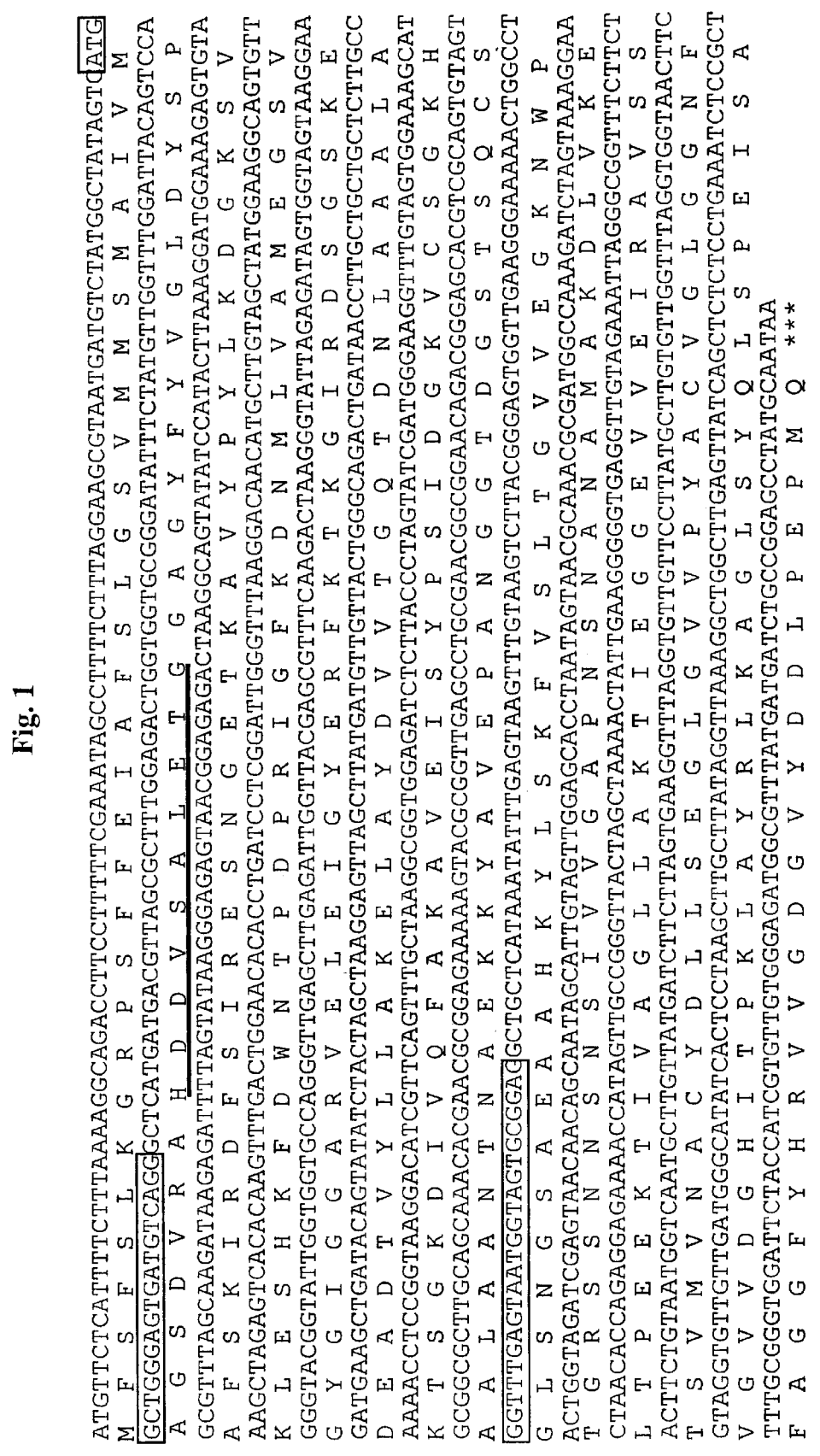

FIG. 1 show the amino acid sequence, SEQ ID NO: 2, of the P44 protein and a nucleotide sequence, SEQ ID NO: 1 which encodes the P44 protein. The deduced amino acid sequence of P44 is shown beneath the DNA sequence. N terminal amino acid sequence of native isolated P44 is underlined. Arrowheads indicate 5' annealing positions of the primer pair (24 mers for forward and 26 mers for reverse) designed for PCR amplification of partial P44 gene which was subcloned into pET30A, an expression vector.

FIG. 2 show the amino acid sequence, SEQ ID NO:4, of the P44-2 protein and a nucleotide sequence, SEQ ID NO:3, which encodes the P44-2 protein.

FIG. 3 show the amino acid sequence, SEQ ID NO:6, of the 144-12 protein and a nucleotide sequence, SEQ ID NO:5. which encodes the P44-12 protein.

FIG. 4 show the amino acid sequence, SEQ ID NO:8, of the P44-15 protein and a nucleotide sequence, SEQ ID NO:7, which encodes the P44-15 protein.

FIG. 5 show the amino acid sequence, SEQ ID NO:10, of the P44-18 protein and a nucleotide sequence, SEQ ID NO:9, which encodes the P44-18 protein.

FIG. 6 show the amino acid sequence, SEQ ID NO:12, of the P44-19 protein and a nucleotide sequence, SEQ ID NO:11, which encodes the P44-19 protein.

Figure 10:
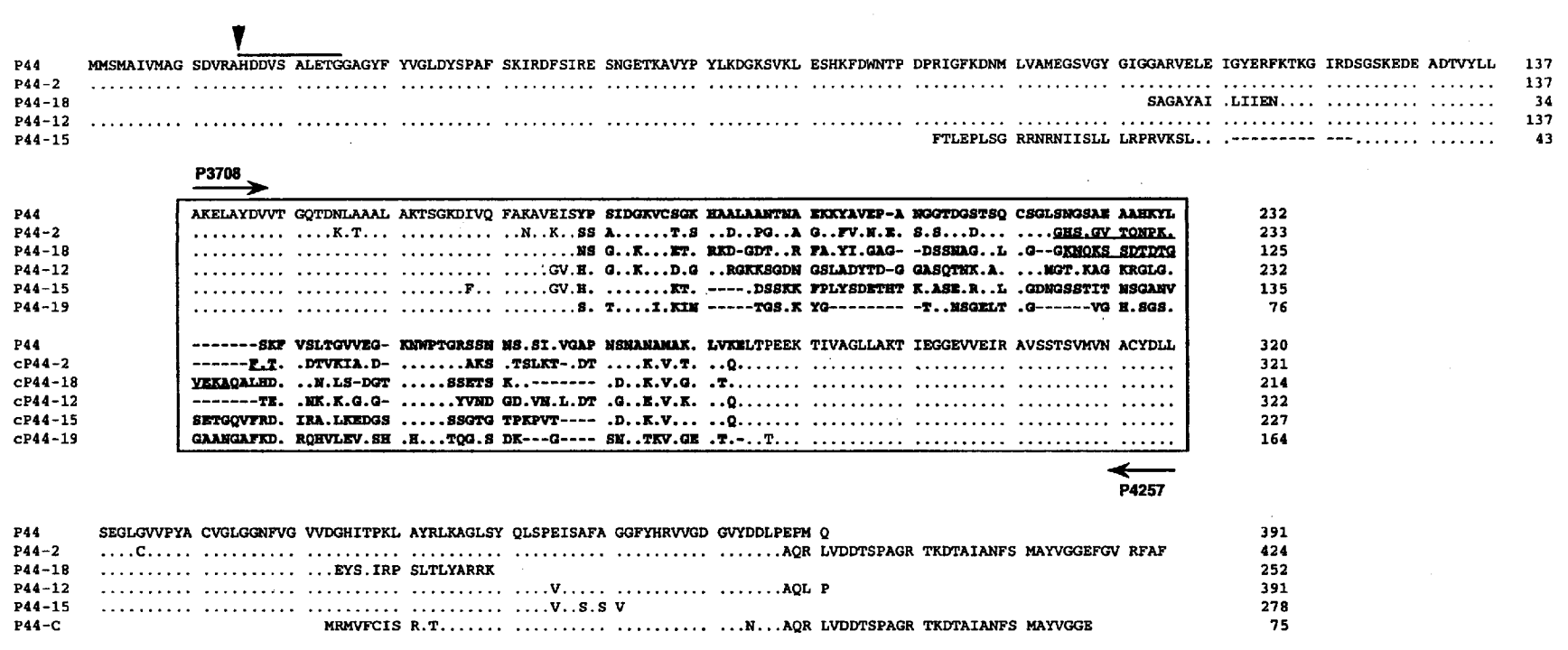

FIG. 10. is an alignment of amino acid sequences of the P44 protein, the P44-2 protein, the P44-18 protein, the P44-12 protein, the P44-15 protein and the P44-19 protein, SEQ ID Nos. 2, 4, 10, 6, 8, and 12, respectively, which were deduced from cDNA clones and the corresponding p44-homologous genes of the HGE agent. Aligned positions of identical amino acids with the P44 protein are shown with dot. Gaps indicate by dashed lines were introduced for an optimal alignment of all proteins. A boxed area in the middle indicates the amino acid sequences deduced from nucleotide sequences of cDNAs. Hypervariable regions are shown in boldface. A bar indicates the N-terminal amino acid'sequence of the native P44 protein and an arrowhead shows the cleavage site of the putative signal peptide. The amino acid sequences underlined in the hypervariable regions of P44-2 and P44-1 8 indicate the sequences which were used to prepare synthetic -oligopeptides, Pep2 and Pep18, respectively. The arrows point out the positions of the primers used in RT-PCR. The numbers on the right side indicate the positions of amino acid residues in P44-homologous proteins from the N terminus to C terminus.

DETAILED DESCRIPTION OF THE INVENTION

Figure 7:
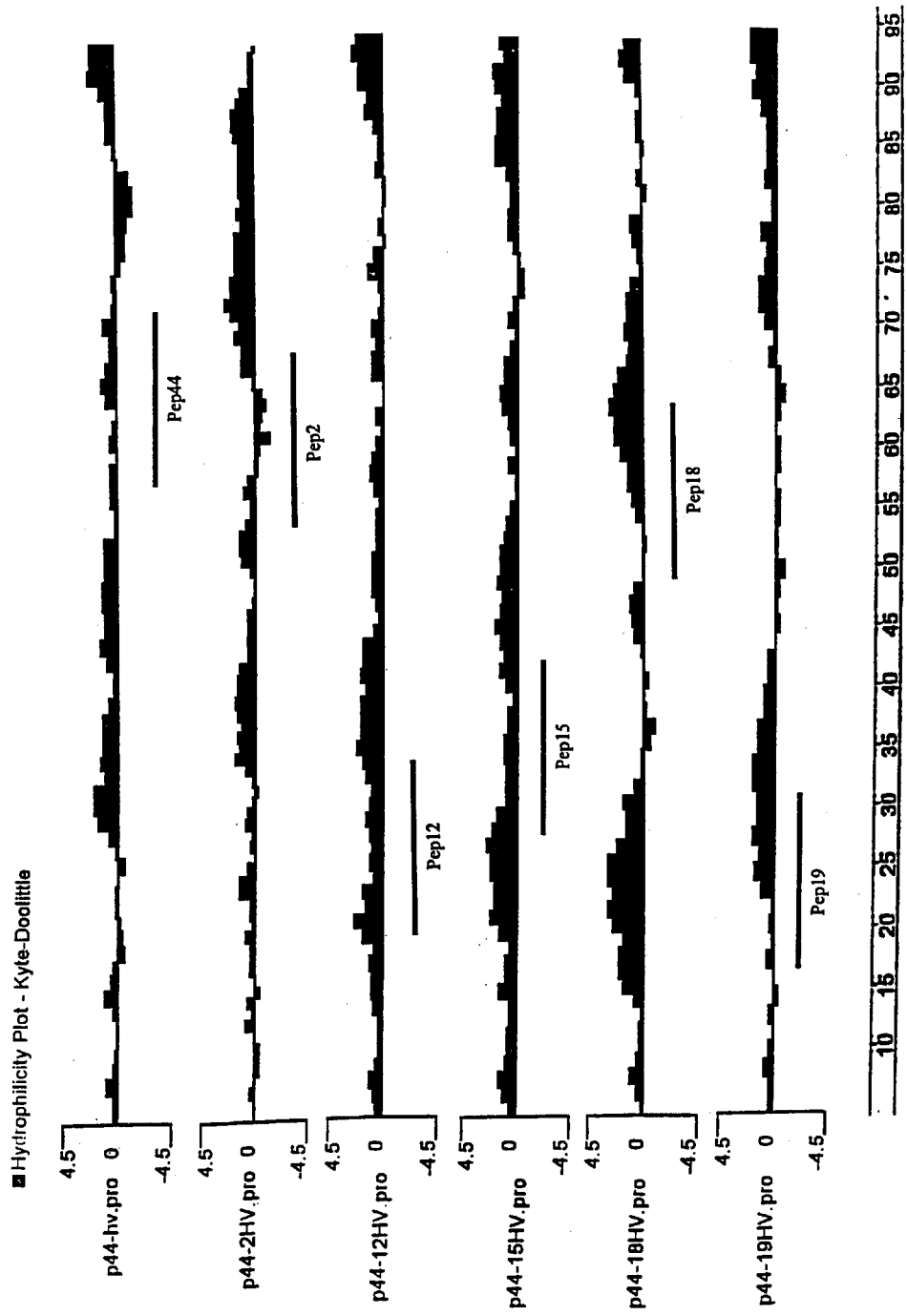
FIG. 7. depicts the hydrophilicity profiles of the Group 44 proteins.
Figure 8:
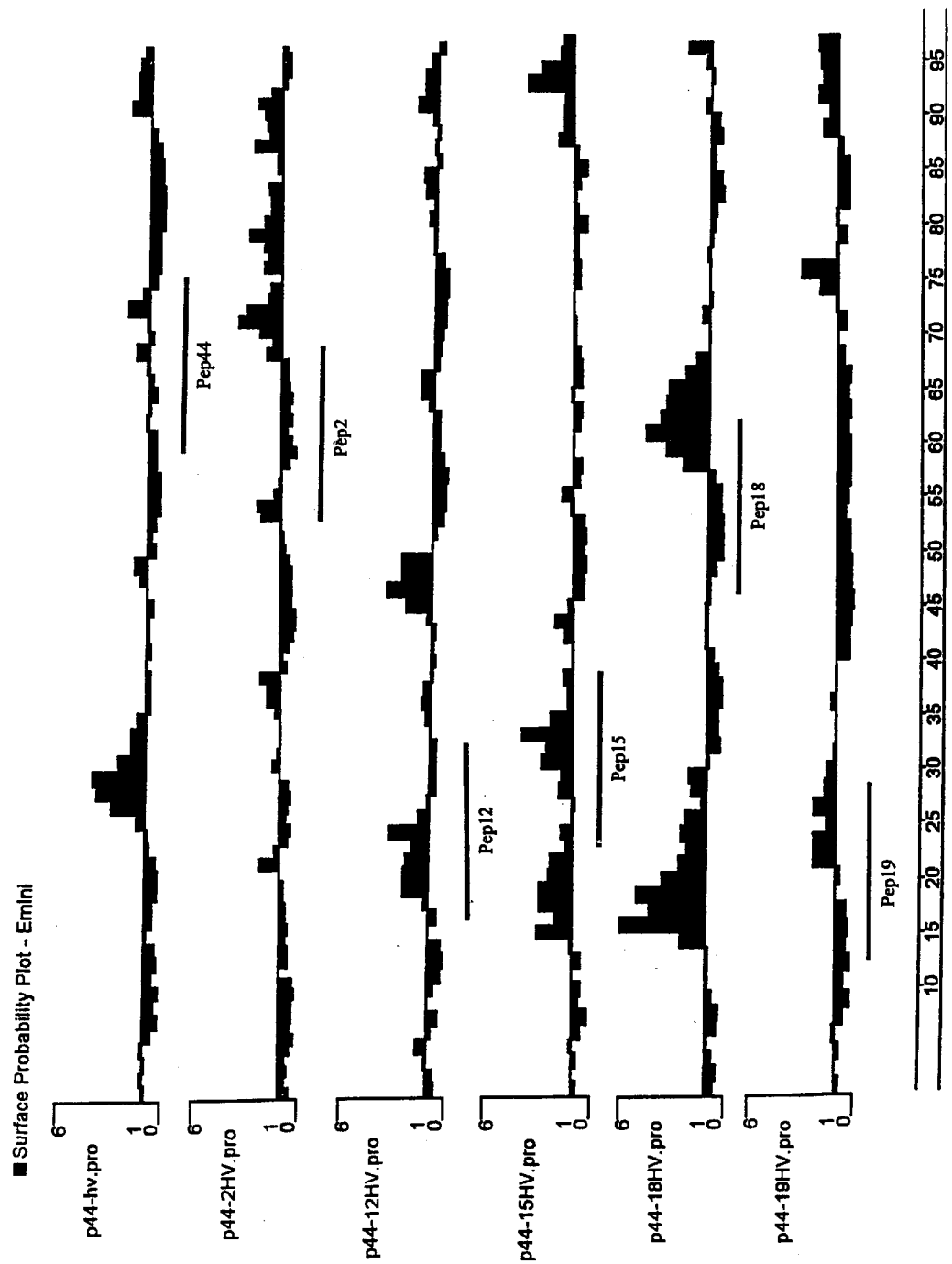
FIG. 8. depicts the antigenic index profiles of the Group 44 proteins.
Figure 9:
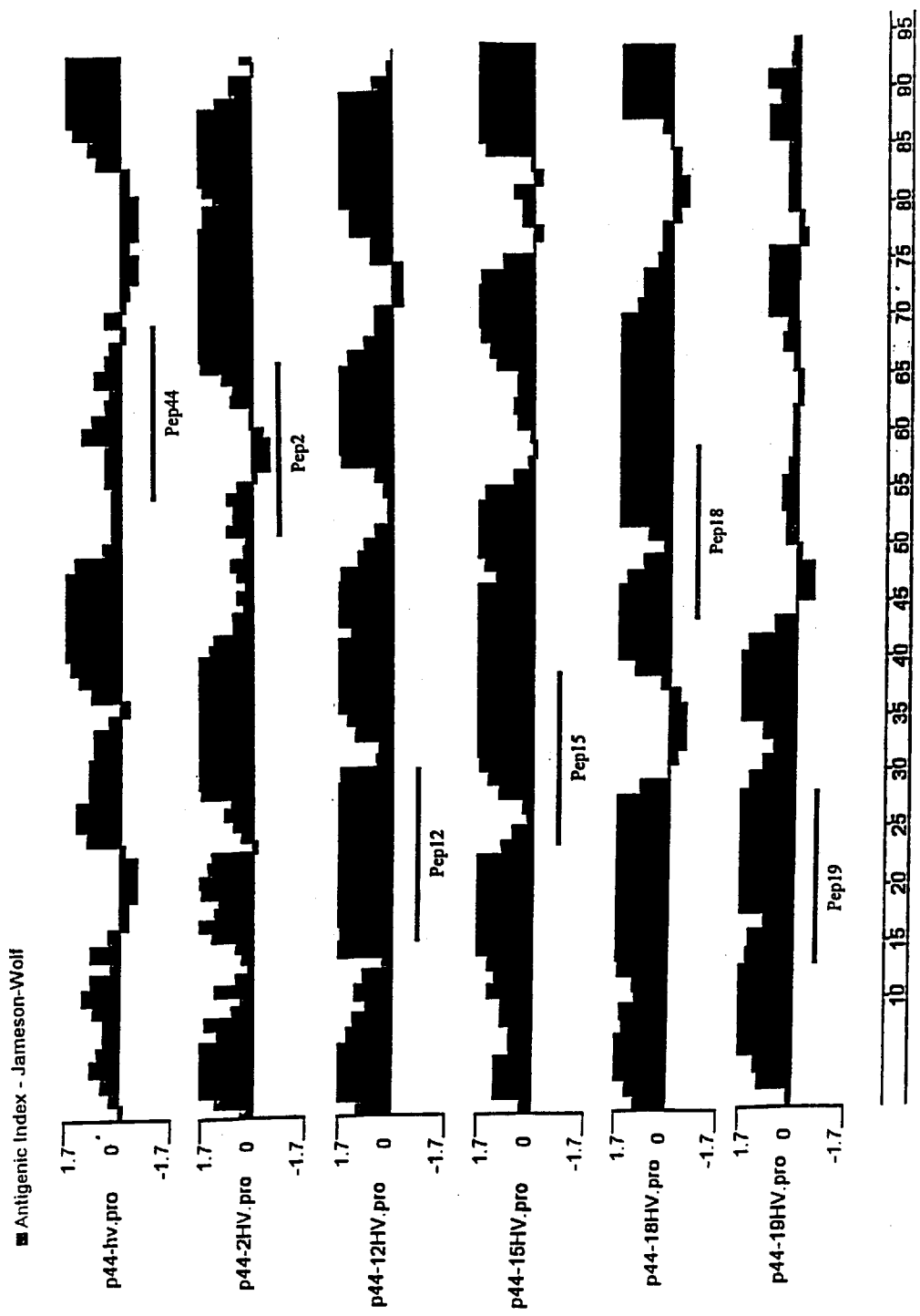
FIG. 9. shows the surface probability profiles of the Group 44 proteins.

The present invention provides a group of structurally related proteins, the Group 44 proteins, which are encoded by a group of homologous genes which are contained within the genome of the HGE causative agent. The Group 44 proteins have an amino acid sequence identity, as determined using the MEGALIGN project in the DNASTAR program (DNA STAR, Inc., Madison, Wis.), ranging from 59% to 83.4%. The Group 44 proteins comprise a single central hypervariable region of about 94 amino acid residues, a first conserved region of about 52 amino acids which is linked either directly or through a linker of from 1 to about 10 amino acids to the amino or N-terminus of the hypervariable region, and a second conserved region of about 56 amino acids which is linked either directly or through a linker of from 1 to about 10 amino acids to the carboxy or C-terminus of the hypervariable region. The Group 44 proteins also comprise an N-terminal end sequence which is linked to the N-terminal amino acid of the first conserved region and a C terminal end sequence which is linked to the C-terminal amino acid of the second conserved region. The Group 44 proteins comprise the P44 protein and variants thereof, the P44-2 protein and variants thereof, the P44-15 protein and variants thereof, the P44-18 protein and variants thereof, and the P44-19 protein and variants thereof.

The hypervariable regions of the Group 44 proteins have a higher hydrophilicity, a higher antigenic index, and a higher surface probability than either the first conserved region or the second conserved regions. The hypervariable regions of the Group 44 proteins have an average hydrophilicity index from about 0.45 to about 0.95, as determined using the Kyte-Doolitle hydrophilicity profile which is described in Kyte, Jack and R. F. Doolitle (1982). J. Mol. Biol. 157:105–132. The hypervariable regions of the Group 44 proteins have an average antigenic index of from about 0.65 to about 1.5, as determined using the Jameson-Wolf antigenic index profile, which is described in Jameson, B. A. and H. Wolf (1988) CABIOS. 4:181–186. The hypervariable regions of the Group 44 proteins have an average surface probability index of from about 1.0 to about 1.55 as determined using the Emini surface probability profile, which is described in Emini, E. A. et al (1985) J. Virology. 55:836–839. The hypervariable regions of the Group 44 proteins have an Mr of from about 8.6 kDa to about 10.9 kDa and an isoelectric point (pI) of from about 7.1 to about 9.2. The hypervariable regions of the Group 44 proteins comprise a first semiconserved region at their N-terminus and a second semiconserved region at their C-terminus. The first semiconserved region comprises the sequence Ile, X1, X2, Lys, X3, Cys wherein X1 is Asp or Gly, X2 is Gly or Lys, and X3 is Val or Ile. The second semiconserved region comprises the sequence Asn, Ala, X1, X2, X3, Ala, X4, X5, Leu, X6, and X7 wherein X1 is Asn, Thr, Lys, or Glu, X2 is Ala or Lys, X3 is Met or Val; X4 is Lys, Gly, or Thr; X5 is Asp or Glu; X6 is Val or Thr, and X7 is Gln or Lys. The hypervariable regions of the Group 44 proteins also comprise a third semiconserved region which is located between the first semiconserved region and the second semiconserved region. The third semiconserved region comprises the sequence Lys-X1-Trp-Pro-Thr-X2; wherein X1 is Asn or His and X2 is Gly, Thr, or Ser. It is believed that the third semiconserved region permits adhesion of the HGE agent to other cells. The characteristics of the hypervariable regions of individual Group 44 proteins are shown in Table 1 below:

TABLE 1

Characteristics of hypervariable regions of Group 44 Proteins

| Group 44 Proteins Hv | Total Mr | Mr of hyper- variable region | Pl. of hyper variable region | Kyte- hydro[a] | James- antige[b] | Emini- surface[c] |
|---|---|---|---|---|---|---|
| P44-hv | 41,293 | 10,327 | 9.16 | 0.45 | 0.65 | 1.0 |
| P44-2hv | 44,969 | 10,454 | 7.17 | 0.53 | 1.29 | 1.03 |
| P44-12hv | 41,197 | 10,378 | 8.17 | 0.82 | 1.38 | 1.04 |
| P44-15hv | 29,287 | 10,831 | 8.77 | 0.82 | 1.37 | 1.25 |
| P44-18hv | 26,400 | 10,186 | 8.65 | 0.94 | 1.49 | 1.53 |
| P44-19hv | | 8,645 | 8.8 | 0.67 | 1.07 | 1.05 |

[a]Kyte-Doolittle hydrophilicity. Kyte, Jack And R. F. Doolittle (1982). A simple method for displaying the hydropathic character of a protein. J. Mol. Biol. 157: 105–132.
[b]Jameson-Wolf antigenic index. Jameson, B. A. and H. Wolf (1988). The antigenic index: a novel algorithm for predicting antigen determinants. CABIOS. 4: 181–186.
[c]Emini surface probability. Emini, E. A. and J. Hughes, D. Perlow and J. Boger (1985). Induction of hepatits A virus-neutralizing and antibody by a virus specific synthetic peptide. J. Virology. 55: 836–839.

The present invention also encompasses variants of the proteins of the Group 44 proteins whose amino acid sequences are shown in SEQ ID Nos 2, 4, 6, 8, 10, and 12. A "variant" as used herein, refers to a protein whose amino acid sequence is similar to the amino acid sequence of a particular Group 44 protein, hereinafter referred to as the reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 90% identical to the reference sequence, preferably, at least 95% identical, more preferably at least 96% identical, most preferably at least 97% identical to the reference sequence. Variant sequences which are at least 90% identical have no more than 10 alterations, i.e any combination of deletions, insertions or substitutions, per 100 amino acids of the reference sequence. Percent identity is determined by comparing the amino acid sequence of the variant with the reference sequence using MEGALIGN project in the DNA STAR program.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Preferably, the amino acid sequence of the first conserved region is at least 95% identical, more preferably at least 97% identical, most preferably at least 98% identical to the amino acid sequence of the first conserved region of P44, P44-2, P44-15, P44-18, or P44-19. Preferably, the amino acid sequence of the second conserved region is at least 95% identical, more preferably at least 97% identical, most preferably at least 98% identical to the amino acid sequence of the second conserved region of P44, P44-2, P44-15, P44-18, or P44-19.

The alterations are designed not to abolish the immunoreactivity of the variant with antibodies that bind to the reference protein. Guidance in determining which amino acid residues may be substituted, inserted or deleted without abolishing such immunoreactivity of the variant protein are found using computer programs well known in the art, for example, DNASTAR software. Preferably, the alterations are not located in the variant protein regions which correspond to the first conserved region or the second conserved region of the respective Group 44 protein The present invention also encompasses fusion proteins in which a tag or one or more amino acids, preferably from about 2 to 15 amino acids, more preferably from about 34 to about 62 amino acids are added to the amino or carboxy terminus of the amino acid sequence of a Group 44 protein or a variant of such protein. Typically, such additions are made to stabilize the resulting fusion protein or to simplify purification of an expressed recombinant form of the corresponding P44 protein or variant of such protein. Such tags are known in the art. Representative examples of such tags include sequences which encode a series of histidine residues, the Herpes simplex glycoprotein D, or glutathione S-transferase.

The present invention also encompasses Group 44 proteins in which one or more amino acids, preferably no more than 10 amino acids, in the respective Group 44 protein are altered by posttranslation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking gamma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

One Group 44 protein is the P44 protein, which weighs approximately 41 kDa and has an isoelectric point of 5.11. The P44 protein and variants thereof specifically bind to antibodies found in the sera from horses infected with the HGE agent and to antibodies in the sera from humans infected with the HGE agent and horse anti-*Ehrlichia equi* serum. The P44 protein does not bind to antibodies in sera from patients infected with *E. chaffeensis* or *Borrelia burgdorferi*. The P44 protein comprises the amino acid sequence, SEQ ID NO: 2, shown in FIG. 1. The hypervariable region of the P44 protein extends from amino acid 176 to amino acid 277 of the sequence, SEQ ID NO:2, shown in FIG. 1. The hypervariable region of the P44 protein and variants thereof have an Mr of from about 8.6 to about 10.8 kDa. The first conserved region of the P44 protein extends from 124 amino acid to amino acid 184 of SEQ ID NO: 2. The second conserved region of the P44 protein extends from amino acid 114 to amino acid 175 of SEQ ID NO:2. The first semiconserved region of the hypervariable region of the P44 protein has the amino acid sequence IDGKVC; the second semiconserved region of the hypervariable region of the P44 protein NANAMAKDLVK, SEQ ID NO: 13; the third semiconserved region of the hypervariable region of the P44 protein has the amino acid sequence KNWPTG.

The P44-2 protein has an Mr of about 45 kDa and an isoelectric point of 5.20. The P44-2 protein comprises the amino acid sequence, SEQ ID NO: 4 shown in FIG. 2. The hypervariable region of the P44-2 protein extends from amino acid 176 to amino acid 277 and has the characteristics shown in Table 1. The first conserved region of the P44-2 protein extends from amino acid 114 to amino acid 175 of SEQ ID NO: 4. The second conserved region of the P44-2 protein extends from amino acid 278 to amino acid 344 of SEQ ID NO: 4. The first semiconserved region of the hypervariable region of the P44 protein has the amino acid sequence IDGKVC; the second semiconserved region of the hypervariable region of the P44-2 protein has the amino acid sequence NAKAVATDLVQ, SEQ ID NO: 14; the third semiconserved region of the hypervariable region of the P44-2 protein has the amino acid sequence KNWPTG.

The P44-12 protein has an Mr of about 41.2 kDa and an isoelectric point of 5.19. The P44-12 protein comprises the amino acid sequence, SEQ ID NO:6, shown in FIG. 3. The hypervariable region of the P44-12 protein extends from amino acid 176 to amino acid 279 and has the characteristics shown in Table 1. The first conserved region of the P44-12 protein extends from amino acid 114 to amino acid 175 of SEQ ID NO: 6. The second conserved region of the P44-12 protein extends from amino acid 280 to amino acid 345 of SEQ. ID. NO. 6. The first semiconserved region of the hypervariable region of the P44-12 protein has the amino acid sequence IDKKVC; the second semiconserved region of the hypervariable region of the P44-12 protein has the amino acid sequence NAEAVAKDLVQ, SEQ ID NO: 15; the third semiconserved region of the hypervariable region of the P44-12 protein has the amino acid sequence KNWPTS.

The P44-15 protein comprises a hypervariable region having an Mr of about 10.8 kDa and an isoelectric point of about 8.8. The P44-15 protein comprises the amino acid sequence, SEQ ID NO:8, shown in FIG. 4. The hypervariable region of the P44-15 protein extend s from amino acid 82 to amino acid 184 and has the characteristics shown in Table 1 below. The first conserved region of the P44-15 protein extends from amino acid 30 to amino acid 83 of SEQ ID NO: 8. The second conserved region of the P44-15 protein extends from amino acid 185 to amino acid 250 of SEQ. ID. 8. The first semiconserved region of the hypervariable region of the P44-15 protein has the amino acid sequence IDGKVC; the second semiconserved region of the hypervariable region of the P44-15 protein has the amino. acid sequence NAKAVAKDLVQ, SEQ ID NO: 16; the third semiconserved region of the hypervariable region of the P44-2 protein has the amino acid sequence KNWPTS.

The P44-18 protein comprises a hypervariable region having an Mr of about 10.2 kDa and an isoelectric point of about 8.7. The P44-8 protein comprises the amino acid sequence, SEQ ID NO:10, shown in FIG. 5. The hypervariable region of the P44-18 protein extends from amino acid 73 to amino acid 170 of the sequence shown in SEQ ID NO: 10. The first conserved region of the P44-48 protein extends from amino acid 21 to amino acid 72 of SEQ ID NO:10. The second conserved region of the P44-18 protein extends from amino acid 171 to amino acid 237 of the SEQ. ID. NO. 10. The first semiconserved region of the hypervariable region of the P44-18 protein has the amino acid sequence IGKKVC; the second semiconserved region of the hypervariable region of the P44-18 protein has the amino acid sequence NAKAVAGDLTK, SEQ ID NO: 17; the third semiconserved region of the hypervariable region of the P44-18 protein has the amino acid sequence KNWPTS.

The P44-19 protein comprises a hypervariable region having an Mr of about 8.6 kDa and an isoelectric point of about 8.8. The P44-19 protein comprises the amino acid sequence, SEQ ID NO: 12. shown in FIG. 6. The hypervariable region of the P44-19 protein extends from amino acid 39 to amino acid 133. The first conserved region of the P44-19 protein extends from amino acid I to amino acid 38 of SEQ ID NO: 12. The second conserved region of the P44-19 protein extends from amino acid 134 to amino acid 164. The first semiconserved region of the hypervariable region of the P44-15 protein has the amino acid sequence IDGKIC; the second semiconserved region of the hypervariable region of the P44-19 protein has the amino acid sequence NATKVAGELTK, SEQ ID NO: 18; the third semiconserved region of the hypervariable region of the P44-19 protein has the amino acid sequence KHWPTT.

The members of the P44 family of proteins are immunogenic and, thus, are useful for preparing antibodies. Such antibodies are useful for immunolabeling isolates of the HGE agent and for detecting the presence of the HGE agent in body fluids, tissues, and particularly in neutrophils. The isolated proteins of the P44 family, particularly P44 are useful for detecting antibodies to the HGE agent in the blood of patients with clinical signs of HGE. The isolated members of the P44 family are also useful in a vaccine for protecting against infection with the HGE agent.

In another aspect, the present invention provides an isolated peptide which comprises a fragment of the P44 protein, hereinafter referred to as rP44 polypeptide. rP44 polypeptide weighs approximately 23 kDa and comprises the amino-terminal half of the P44 protein. In one embodiment, rP44 comprises the amino acid sequence extending from amino acid 30 through amino acid 248 of the amino acid sequence shown in FIG. 1. In another embodiment the rP44 comprises the amino acid sequence extending from amino acid 38 through amino acid 248 of the amino acid sequence shown in FIG. 1, and, thus, lacks the amino acids of the signal sequence of the P44 protein. The rP44 peptide is a useful diagnostic tools for detecting the presence of antibodies in the bodily fluids, particularly sera, of individuals infected with the causative agent of HGE.

The present invention provides oligopeptides of from about 14-16 amino acids in length and having a sequence which is specific to one or more of the P44 family proteins. Such peptides are useful for preparing chimeric peptides that are used to prepare antibodies that are immunospecific for one or more, of the P44 family proteins. In one embodiment, the synthetic oligopeptide comprises the amino acid sequence LSNGSAEAAHKYLSK, SEQ ID NO:19, which is specific for the P44 protein. In another embodiment, the synthetic oligopeptide comprises the amino acid sequence GHSSGVTQNPKLFST, SEQ ID NO20, which is specific for the P44-2 protein. In another embodiment, the synthetic oligopeptide comprises an amino acid sequence GKKSGDNGSLADYTD, SEQ ID NO:21, which is specific for the P44-12 protein. In another embodiment, the synthetic oligopeptide comprises an amino acid sequence PLYSDETHTKGASEGR, SEQ ID NO:22, which is specific for the P44-15 protein. In another embodiment, the synthetic oligopeptide comprises the amino acid sequence KNQKSSDTDTGVEKA, SEQ ID NO:23, which is specific for the P44-18 protein. In another embodiment, the synthetic oligopeptide comprises the amino acid sequence TGSNKYGTGTNSGELT, SEQ ID NO:24, which is specific for the P44-19 protein.

The present invention also provides isolated polynucleotides or nucleic acids which encode the proteins of the P-44 family or variants of the P44 family proteins. The polynucleotide is a DNA or RNA molecule, preferably a DNA molecule, and comprises a sequence which codes for a Group 44 protein or a variant thereof One polynucleotide, referred to hereinafter as the p44 polynucleotide" encodes the P44 protein. In one embodiment, the p44 polynucleotide comprises the nucleotide sequence, SEQ ID NO. 1, shown in FIG. 1. Another polynucleotide, the p44-2 polynucleotide encodes the P44-2 protein. In one embodiment the p44-2 polynucleotide comprises the nucleotide sequence, SEQ ID NO: 3 shown in FIG. 2. Another polynucleotide, the p 44-12 polynucleotide encodes the P44-12 protein. In one embodiment the p44-12 polynucleotide comprises the nucleotide sequence, SEQ ID NO: 5, shown in FIG. 3. Another polynucleotide, the p 44-15 polynucleotide encodes the P44-15. protein. In one embodiment the p44-15 polynucleotide comprises the nucleotide sequence, SEQ ID NO: 7, shown in FIG. 4. Another polynucleotide, the p44-18 polynucleotide encodes the P44-18 protein. In one embodiment the p44-18 polynucleotide comprises the nucleotide sequence, SEQ ID NO: 9, shown in FIG. 5. Another polynucleotide, the p44-19 polynucleotide encodes the P44-19 protein. In one embodiment the p44-19 polynucleotide comprises the nucleotide sequence, SEQ ID NO: 11, shown in FIG. 6.

Polynucleotides that encode the Group 44 proteins are useful tools that can be used in recombinant techniques for producing the Group 44 proteins. Polynucleotides encoding the Group 44 proteins are also useful for designing hybridization probes for isolating and identifying cDNA clones and genomic clones encoding the Group 44 proteins or allelic forms thereof. Such hybridization techniques are known to those of skill in the art. Sequence of polynucleotides that encode the Group 44 proteins are also useful for designing primers for polymerase chain reaction (PCR), a technique useful for obtaining large quantities of cDNA molecules that encode the Group 44 proteins.

Also encompassed by the present invention, are single stranded polynucleotides, hereinafter referred to as antisense polynucleotides, having sequences which are complementary to the DNA and RNA sequences which encode the P44 protein, the P44-2 protein, the P44-15 protein, the P44-18 protein, and the P44-19 protein. The term complementary as used herein refers to the natural binding of the polynucleotides under permissive salt and temperature conditions by base pairing, The present invention also encompasses oligonucleotides that are used as primers in polymerase chain reaction (PCR) technologies to amplify transcripts of the genes which encode the P44 family proteins or portions of such transcripts. Preferably, the primers comprise 18–30 nucleotides, more preferably 19–25 nucleotides. Preferably, the primers have a G+C content of 40% or greater. Such oligonucleotides are at least 98% complementary with a portion of the DNA strand, i.e., the sense strand, which encodes the respective P44 family protein or a portion of its corresponding antisense strand. Preferably, the primer has at least 99% complementarity, more preferably 100% complementarity, with such sense strand or its corresponding antisense strand. Primers which are which have 100% complementarity with the antisense strand of a double-stranded DNA molecule which encodes a P44 family protein have a sequence which is identical to a sequence contained within the sense strand. The identity of primers which are 15 nucleotides in length and have full complementarity with a portion of the antisense strand of a double-stranded DNA molecule which encodes the P44 protein is determined using the nucleotide sequence, SEQ ID NO:1, shown in FIG. 1A and described by the general formula a-b, where a is any integer between 1 to 1239, where b is equal to a+14, and where both a and b correspond to the positions of nucleotide residues shown in SEQ ID NO: 1.

The present invention also encompasses oligonucleotides that are useful as hybridization probes for detecting transcripts of the genes which encode the P44 family proteins or for mapping of the genes which encode the P44 family proteins Preferably, such oligonucleotides comprise at least 210 nucleotides, more preferably at least 230, most preferably from about 210 to 280 nucleotides. Such hybridization probes have a sequence which is at least 90% complementary with a sequence contained within the sense strand of a DNA molecule which encodes a P44 family protein or with a sequence contained within its corresponding antisense strand. Such hybridization probes bind to the sense strand under stringent conditions. The term "stringent conditions" as used herein is the binding which occurs within a range from about Tm 5° C. (5° C. below the melting temperature Tm of the probe) to about 20° C. to 25° C. below Tm. The probes are used in Northern assays to detect transcripts of p44 homologous genes and in Southern assays to detect p44 homologous genes. The identity of probes which are 200 nucleotides in length and have fill complementarity with a portion of the antisense strand of a double-stranded DNA molecule which encodes the P44 protein is determined using the nucleotide sequence, SEQ ID NO: 2, shown in FIG. 1A and described by the general formula a-b, where a is any integer between 1 to 1239, b is equal to a +200, and where both a and b correspond to the positions of nucleotide residues shown in SEQ ID NO:1.

The present invention also encompasses isolated polynucleotides which are alleles of the genes which encode the Group 44 proteins. As used herein, an allele or allelic sequence is an alternative form of the gene which may result from one or more mutations in the sequences which encode the Group 44 proteins. Such mutations typically arise from natural addition, deletion of substitution of nucleotides in the open reading frame sequences Any gene may have none, one, or several allelic forms. Such alleles are identified using conventional techniques, such as for example screening libraries with probes having sequences identical to or complementary with one or more Group 44 polynucleotides.

The present invention also encompasses altered polynucleotides which encode Group 44 proteins or Group 44 protein variants. Such alterations include deletions, additions, or substitutions. Such alterations may produce a silent change and result in a Group 44 protein having the same amino acid sequence as the Group 44 protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 1–6 to increase the rate of expression of the proteins encoded by such sequences. Such alterations may also introduce new restriction sites into the sequence or result in the production of a Group 44 protein variant. Typically, such alterations are accomplished using site-directed mutagenesis.

In another aspect, the present invention relates to antibodies which are specific for and bind to at least one Group 44 protein or a peptide specific for one or more Group 44 proteins. Such antibodies are useful research tools for identifying cells, particularly granulocytes, infected with the causative agent of HGE and for purifying the major outer membrane protein of the causative agent of HGE from partially purified preparations by affinity chromatography. Such antibodies are also useful for identifying bacterial colonies, particularly colonies of genetically-engineered bacteria, that are expressing the major outer membrane protein of the causative agent of HGE.

The present invention also relates to kits containing reagents for diagnosing HGE. The kit comprises one or more Group 44 proteins or antigenic fragments thereof. Preferably, the kit comprises a panel of Group 44 proteins or peptide fragments thereof. For ease of detection, it is preferred that the Group 44 proteins or peptides be attached to a substrate such as a column, plastic dish, matrix, or membrane, preferably nitrocellulose. The kit may further comprise a biomolecule, preferably a secondary antibody, for detecting interactions between the isolated Group 44 protein or peptide and antibodies in a patient sample. Preferably, the biomolecule is coupled to a detectable tag such as an enzyme, chromophore, fluorophore, or radioisotope. The kit is used by contacting a patient sample with the Group 44 proteins or peptides under conditions that permit formation of antigen-antibody complexes. Then the biomolecule is added and the presence or absence of any resulting antigen-antibody complexes is detected by assaying for a change in the sample, for example, by observing the formation of a precipitate in the sample, the presence of radioactivity on the substrate, or a color change in the sample or on the substrate.

The present invention also provides a method for detecting antibodies to the HGE agent in a sample of a bodily fluid from a patient. The method comprises providing one or more Group 44 proteins or antigenic fragments thereof, contacting the Group 44 protein or antigenic fragment thereof with a bodily sample taken from the patient; and assaying for the formation of a complex between Group 44 protein or antigenic fragment thereof and antibodies in the bodily sample. The sample may be a tissue or a biological fluid, including urine, whole blood, or exudate, preferably serum. The sample may be untreated, subjected to precipitation, fractionation, separation, or purification before combining with the Group 44 protein. Interactions between antibodies in the sample and the Group 44 protein are detected by radiometric, calorimetric, or fluorometric means, size-separation, or precipitation. Preferably, detection is by addition of a secondary antibody that is coupled to a detectable tag, such as for example, an enzyme, fluorophore, or chromophore.

Formation of the antigen-antibody complex is indicative of the presence of anti-HGE antibodies, either IgM or IgG, in the patient. Thus,.the method is used to determine whether a patient is infected with the HGE agent. The method can also be used to distinguish patients infected with HGE from patients infected with *Ehrlichia chaffeensis* or *Borrelia burgdorferi* as there is no cross-reactivity between the isolated Group 44 proteins, particularly the P44 protein or the rP44 polypeptide, and antibodies produced in individuals infected with either *Ehrlichia* chaffeensis or *Borrelia burgdorferi*.

Preparing the Group, 44 Proteins and Pentides

The Group 44 proteins, the rP44 polypeptide, and the synthetic P44 oligopeptides may be produced by conventional peptide synthesizers. The Group 44 proteins and rP44 polypeptide may also be produced using cell-free translation systems and RNA molecules to derived from DNA constructs that encode the Group 44 proteins and the rP44 polypeptide. Alternatively, the Group 44 proteins and the rP44 polypeptide are made by transfecting host cells with expression vectors that comprise a DNA sequence that encodes the respective Group 44 protein or the rP44 polypeptide and then inducing expression of the protein or polypeptide in the host cells. For recombinant production, recombinant constructs comprising one or more of the sequences which encode the respective Group 44 protein or rP44 peptide are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The Group 44 proteins and rP44 polypeptide may be expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the P44 protein or rP44 polypeptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate recombinant Group 44 proteins or rP44 polypeptide.

Synthetic oligopeptides specific for a particular Group 44 protein are identified by examining and comparing the hypervariable regions of the known Group 44 proteins.

Preparation of Antibodies

The Group 44 proteins, the rP44 polypeptide, and the P44 synthetic oligopeptides are used as immunogens to produce antibodies immunospecific for one or more Group 44 proteins. The term "immunospecific" means the antibodies have substantially greater affinity for one or more Group 44 proteins than for other proteins. Such antibodies may include, but are not limited to, polyclonal, monoclonal, chimeric, single chain, and Fab fragments.

It is preferred that the peptides, fragments, or oligopeptides that are used to induce antibodies to the P44 family proteins have an amino acid sequence of at least five amino acids, and more preferably, at least 10 amino acids that are identical to a portion of the amino acid sequence of a Group 44 protein. Preferably, the oligopeptide has a sequence which is identical to a portion of the hypervariable region of a Group 44 protein. Such peptides are conventionally fused with those of another protein such as keyhole limpet hemocyanin and antibody produced against the chimeric molecule.

Polyclonal antibodies are generated using conventional techniques by administering the Group 44 protein or a portion thereof, i.e., the rP44 polypeptide, or the P44 chimeric molecule to a host animal. Depending on the host species, various adjuvants may be used to increase immunological response. Among adjuvants used in humnas, BCG (bacilli Calmette-Guerin, and Corynebacterium parvum are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols which involve competitive binding or immunoradiometric assays and typically involve the measurement of complex formation between the respective Group 44 protein and the antibody.

Polynucleotides that Encode Group 44 Proteins or Variants Thereof

Polynucleotides comprising sequences encoding a Group 44 protein or a variant thereof may be synthesized in whole or in part using chemical methods. Polynucleotides which encode a Group 44 protein, particularly alleles of the genes which encode a Group 44 protein, may be obtained by screening a genomic library of an HGE isolate with a probe comprising sequences identical or complementary to the sequences shown in FIGS. 1–6 or with antibodies immunospecific for a Group 44 protein to identify clones containing such polynucleotide.

The probes are used in Southern blot or colony hybridization assays under high stringency conditions. Alternatively, polynucleotides encoding Group 44 proteins may be made using polymerase chain reaction (PCR) technology and primers which bind specifically to sequences which are known to encode a Group 44 protein.

The following examples are for purposes of illustration only and are not intended to limit the scope of the claims which are appended hereto.

EXAMPLES

Example 1 p44 Polynucleotide

A. Cloning

HGE agent No. 2, 3, 6, 11 and 13 isolates isolated from patients in New York State were cultivated in HL-60 cells. The organisms were purified by the Sephacryl S-1000 chromatography method as described by Rikihisa et al in Analysis of *Ehrlichia canis* and canine granulocytic Ehrlichia infection. J. Clin. Microbiol. 30: 143–148 (1992). Genomic DNA of the HGE agent was isolated from purified ehrlichial organisms by SDS lysis, pronase digestion, phenol-chloroform extraction, and ethanol precipitation, according to the procedure of Ohashi et al (1998). Immunodominant major outer membrane proteins of Ehrlicha chaffeensis are encoded by a polymorphic multigene family. Infect Immun. 66: 132–139. Purified genomic DNA was completely digested with 20 units of EcoRI at 37° C. for 4 h, and then litigated into the λZAPII vector. All procedures were carried out by using λZAPII/EcoRI/CIAP cloning kit (Stratagene, La Jolla, Calif.) according to the manufacturer's instruction. The gene library was constructed by infecting *E. coli* AL1-blue MRF1 strain with the recombinant phage. Clones and strain with the recombinant phage. Clones expressing ehrlichiial proteins were identified by using horse anti-HGE serum which has been preabsorbed with *E. coli* lysate. Positive recombinant pBluescript phagemids were excised from the λZAPII phages in the presence of helper f1 and were used to transform *E. coli* SOL R cells (Stratagene). All of the positive clones were analyzed by Western blotting using the horse anti-HE gent serum. Phagemids purification, restriction enzyme digestion, and gel electrophoresis were carried out as described by Sambrook et at in Molecular cloning: a laboratory manuals. 2nd ed. Cold Spring Harbor Laboratory Press. Plainview, N.Y. (1989).

DNA sequencing was determined by dideoxyl-termination method with an Applied Biosystems 373 DNA sequencer. DNA sequencing was performed by primer-walking method using synthetic oligonucleotides as primers. Translation of the nucleotide sequence and alignment of the amino acid sequence were made by using DNASIS computer software (Hitachi Software Engineering Co. Ltd., Yokohama, Japan). A homology search was done with data base of GenBank (National Center for Biotechnology Information, Bethesda, Md.) by using the software local alignment search tool (Altschul, S. F et al, Basic local alignment search tool. J. Mol. Biol. 215: 403–410. 1990) in the BLAST network service (NCBI). GenBank.

One of the positive clone which expressed a 44-kDa antigenic protein was named pHGE1221. The insert size of pHGE1221 was approximately 6.9 kb. The map of pHGE1221 contained five ORFs and the second ORF of 1239 bp encoding a 413-amino acid protein with a molecular mass of 43,739 Da including signal peptide. This protein was designated the P44 proteinThe nucleotide sequence, SEQ ID NO:1, of ORF2 and the amino acid sequence, SEQ ID NO:2, encoded by ORF2 is shown in FIG. 1. The ORF1 contained 759 nucleotide base pairs encoding 253-amino acids without start codon. Two regions in the ORF1 were found to share the exact same sequences within ORF2. These conserved regions were named R1 and R2, which encoded 59- and 65-amino acids, respectively.

B. p44 Polynucleotide Probe

A 1.2-kb p44 gene fragment generated by PCR from the clone pHGE1221 was labeled with [32P] dATP by the random primer method using a kit (Boehringer Mannheim, Indianapolis, Ind.) and the labeled fragment and used as a DNA probe to detect p44 homologous genes. Genomic DNA (200 ng) extracted from the purified HGE agent HZ strain was completely digested with 20 units of restriction endonucleases at 37° C. for 4 h, electrophoresed, and transferred to Hybond-N+ nylon membrane (Amersham, Arlington Heights, Ill.) by a standard method . Hybridization was 16 h. The nylon sheet was washed in 01.×SSC )1×SSC containing 0.15M sodium chloride and 0.015M sodium citrate) with 1% SDS at 55° C. and hybridized probes were exposed to Hyperfilm (Amsersham) at −80° C. Genomic Southern blot analysis revealed more than 10 bands bound to the p44 gene probe, suggesting the existence of additional p44-homologous genes in the HGE agent genome.

Example 2

Figure 12:
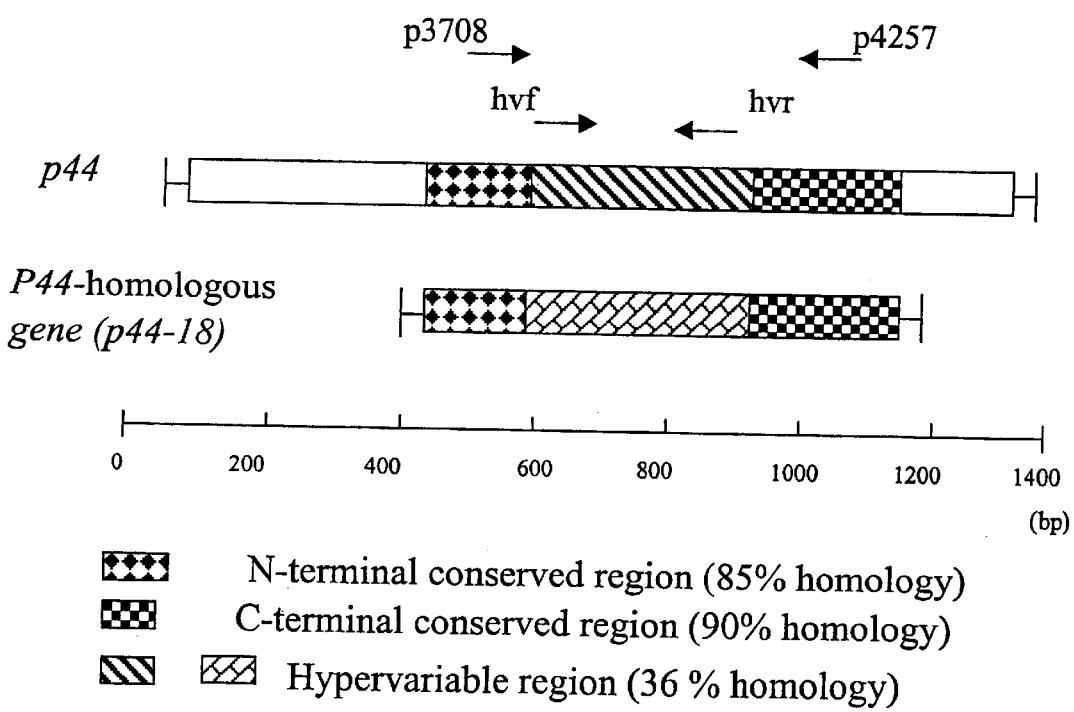
FIG. 12 shows the primer positions in the p44 gene and the truncated ORF homologous to p44 in the recombinant plasmid pHGE1221. The primers p3708 and p4257 were designed for RT-PCR to amplify the cDNA of p44-homologous genes. The primers hvf and hvr were designed to prepare the cDNA-specific probes by PCR for Southern and Northern blot analysis.

Polynucleotides Encoding P44-2 Protein, P44-12 Protein, P44-15 Protein P44-18 Protein. and P44-19 Protein A. RT-PCR and Cloning of cDNAs A pair of oligonucleotides used for RT-PCR (p3708 and p4257 as shown in FIG. 12 and Table 2 below) was designed based on the conserved regions between DNA sequences of the p44 gene and a truncated p44-homologous gene downstream from the p44. Total RNA was extracted from HL-60 cells infected with the HGE agent by d using TRIzol reagent (GIBCO-BRL, Gaithersburg, Md.). The isolated RNA (3 $\mu$g) was heated at 70° C. for 10 min and reverse transcribed in a 20-$\mu$l reaction mixture (0.5 mM deoxynuleoside triphophate mixture (dNTP), 200 U of SuperScript II reverse transcriptase (GIBCO-BRL), 2 pmole of p4257 primer, and 3 mM $MgCl_2$) at 42° C. for 50 min. PCR was performed in a 100-$\mu$l reaction mixture containing 2 $\mu$l of the cDNA product, 10 pmole of each of p3726 and p4257 primers, 0.2 mM dNTP mixture, 5 U of Taq DNA polymerase, and 1.5 mM $MgCl_2$, with 3 min of denaturation at 94° C. followed by 30 cycles consisting of 1 min of denaturation at 94° C., 1 min of annealing at 52° C., and 2 min of extension at 72° C. To rule out contamination of DNA in the RNA preparation, RT-PCR without reverse transcriptase was carried out (negative control). The amplified RT-PCR products were cloned in a pCRII vector by using the TA Cloning Kit (Invitrogen Co., San Diego, Calif.). Twenty five cDNA clones, which were randomly selected from the transformants, were sequenced by dideoxy chain termination method with an Applied Biosystems 373 DNA sequencer.

Figure 11:
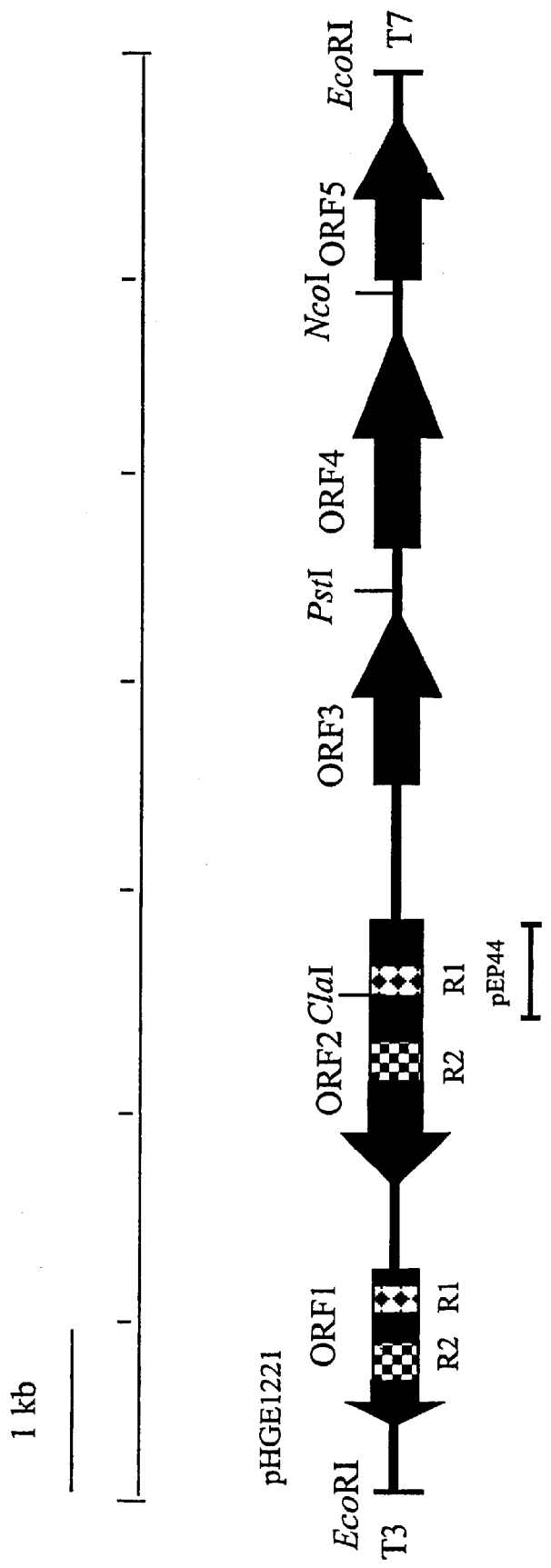
FIG. 11 is a restriction map of 6.9-kb genomic DNA fragment including p44 gene of the HGE agent. The closed boxes with arrow indicate four open reading frames (ORF) which are identified in this fragment. The arrows indicate the orientation of these ORFs. Shaded boxes (R1 and R2) show two regions identical in the ORF1 which encoded 59- and 65-amino acids, respectively. The solid bar at bottom indicates the region which was cloned into the pET30a expression vector.

After cloning the amplicons, only five different nucleotide sequences were found in the 25 randomly selected cDNA. The five sequences of the cDNAs were represented as p44-2 cDNA, p44-18cDNA, p44-12 cDNA, p44-15 cDNA, p44-18 cDNA and p44-19 cDNA. A comparison of the deduced amino acid sequences among then proteins and polypeptides encoded by the five different cDNAs and the p44 gene revealed that a central region of approximately 94-amino acid residues corresponding to the 175th- to 269th-amino acid sequence of the P44 protein was hypervariable, and flanked regions of approximately 30 residues each was highly conserved (FIG. 11). Within the hypervariable region, the highest amino acid sequence similarity was 32.8% between the P44-2 and P44-18 proteins, and the lowest similarity was 19.9% between P44-15 and P44 proteins. In comparison with flanking regions, the hypervariable region had higher hydrophilicity and antigenic index.

The N-terminal amino acid sequence (HDDVSALETG) of the native 44-kDa protein was found in P44, $P_44-_2$ and P44-12 proteins. A comparison of deduced amino acid sequences of these proteins revealed anidentical amino acid sequence consisting of 15 residues at their N terminus. It is believed that this sequence is a signal peptide. The alignment also showed that the N- and C-terminal portions are highly conserved among three Group 4 proteins (P44-2, P44-12 and P44), except existence of additional 34-amino acid residues at C terminus of P44-2 (FIG. 11). At N and C termini of both P44-15 and P44-18 proteins there is a short stretch of an amino acid sequence consisting of 8 to 28 residues without any homology to other Group 44 proteins including P44, P44-2 and P44-12 (FIG. 11).

B. P44-2, p44-12, p44-14, p44-18, and p44-19 Probes

DNA probes specific to each of the cDNAs for Southern blotting were designed based on a comparison of deduced amino acid sequences among these cDNAs. The central hypervariable regions in each cDNA and in the p44 gene were amplified by PCR with primer pairs as shown in Table 2 below. The amplicons were cloned into a pCRII vector. The DNA insert excised from each recombinant plasmid was labeled with [$\alpha$-$^{32}$P]dATP by the random primer method with a kit (Amersham, Arlington Heights, Ill.) and used as a probe to detect genes in the genome of the HGE agent.

DNA Hybridization was performed in a Rapid Hybridization Buffer (Amersham). The membrane was exposed to a Hyperfilm (Amersham). A single DNA band was detected in all restriction digestions tested. Since restriction enzymes used do not cut within a p44 gene and all cDNA clones, this suggests that each gene corresponding to the four probes is a single copy in the HGE agent genome. The probes specific to the cDNAs of P44-2 and P44-15 generated two or three bands, showing that two to three gene copies with sequences identical or highly homologous to those of the cDNAs of P44-2 or P44-15 exist in the HGE agent genome.

The XbaI DNA fragments of the HGE agent, which were detected by genomic Southern blot analysis, were inserted into a pBluescript II KS(+) vector, and the recombinant plasmids were introduced into *Escherichia coli* DH5$\alpha$. By using the colony hybridization method (29) with the specific DNA probes same as those used for Southern blot analysis, three positive clones were isolated and the DNA inserts were sequenced. The clones were designated pHGE3.0, pHGE3.4, and pHGE3.9 containing ehrlichial DNA fragments of 3.0, 3.4, and 3.9 kb, respectively.

Sequencing of the 3.9- and 3.0-kb fragments revealed two complete ORFs of 1,275 bp and 1,173 bp encoding 425- and 391-amino acid proteins with Mr of 44,969 and 41,179, respectively. As expected, these ORFs (p44-2 and p44-12) contained the sequences identical to the cDNAs of P44-2 and P44-12, respectively (FIG. 2, 4The 3.4-kb DNA fragment contained an ORF of 834 bp encoding 278-amino acid protein with Mr of 29,387. This ORF (p44-15) included a sequence identical to P44-15 cDNA. The p44-15 did not have a universal start codon and lacked DNA sequence corresponding to 82-amino acid residues at the N terminus of the P44 protein. Consensus sequences of $\sigma^{70}$ promoter (AT-rich region about 10 base pairs upstream of the transcription start site; the −10 sequence) and Shine-Dalgarno sequence were found in the regions upstream from the start codon of p44-2 and p44-12. The nucleotide sequence(s) of the cDNAs and genes have been submitted to GenBank™/ EBI Data Bank and assigned accession number(s) AF135254, AF135255, AF135256, AF135257, AF135258, AF135259, AF132260, AF132261, AF132262, and AF 132263. The nucleotide sequences of the cDNAs (SEQ ID Nos 3, 5, 7, 9, and 11) and the amino acid sequences, SEQ ID Nos 4, 6, 8, 10, and 12, of the proteins and polypeptides, encoded by the cDNas are shown in FIGS. 2–6.

TABLE 2

Oligodeocynucleotides used in RT-PCR and PCR

| Target Genes | Primers | Nucleotide Sequences (5'-3') | Regions[a] (nt.) | PCR products (pb) | Usage |
|---|---|---|---|---|---|
| | P3708 | GCTAAGGAGTTAGCTTATGAT | 411–432 | | |
| | P4257 | AAGAAGATCATAACAAGCAT | 936–960 | 549 | Cloning of DNA |
| | (hvf and hvr[b] | | | | |
| P44-2 | 2hvf | TACTGGTAGCCATGCTGACC | 542–563 | | |
| | 2hvr | AATCACCCGTCTTCAGTGATG | 769–789 | 231 | Southern/Northern blot |
| P44-18 | 18hvf | GGAGATTTCTAATTCCGGTAT | 542–563 | | |
| | 18hvf | AGTCATTATTCGATTTAGACG | 769–789 | 234 | Southern/Northern blot |
| P44-12 | 12hvf | TGATAAGAAGGTTTGTGATGG | 542–563 | | |
| | 12hvr | AGAGCACATTAACGTTGTCAC | 769–789 | 270 | Southern blot |
| P44-15 | 15hvf | GAAGGTTTGTAAGACGAAGGC | 542–563 | | |
| | 15hvr | AGTTCGTGACAGGTTTTGGAG | 769–789 | 240 | Southern blot |
| P44-19 | 19hvf | CATTGATGGGAAGATTTGTAAG | 542–564 | | |
| | 19hvr | AGGTGAGCTTTGTTAGTTCTC | 769–789 | 234 | Southern blot |
| P44 | 44hvf | GAAGGTTTGTAGTGGAAAGCA | 542–563 | | |
| | 44hvr | ATGCTCCAACTACAATGCTAT | 769–789 | 247 | Southern/Northern blot |
| 3' end of p44-12 | pnfl2 | CAAGTTTGACTGGAACACTCC | 218–239 | | |
| (p44#12n)[c] | pnrl2 | AACAATATCTTTACCAGAGG | 478–498 | 280 | Southern blot |
| 5' end of p44-12 | pcfl2 | CTAAAGACCTAGTACAGGAGC | 880–901 | | |
| (p44-12C)[c] | pcrl2 | GAGAGAGCTGATAACTCAACC | 1072–1093 | 210 | Southern blot |

[a]Numbers correspond to the nucleotides in the p44 gene which was cloned in reference 34 (GenBank accession number: AF059181) and the primer positions are shown in FIG. 1.
[b]Primer pairs are used to amplify hypervariable regions of each of cDNA's.
[c]Probes p44-12N and p44-12C are specific to 5'- and 3'- end conserved regions of p44 homologous genes.

Example 3

P44 Protein and rP44 Polypeptide.

Amino acid sequence analysis of the P44 protein indicated that it is a typical transmembrane protein which contains alternative hydrophilic and hydrophobic motifs with a signal peptide of 37 amino acid residues. Searching of the GenBank database revealed amino acid sequence similarity between the HGE agent P44 and Anaplasma marginale, a bovine intraerythocytic bacteria, major surface protein 2 (66% similarity; 44% identity).

The entire P44 protein was expressed by cloning whole p44 gene into pET30a vector.

However, the expression level is low.

To effectively overexpress antigenic epitopes of recombinant P44, the deduced amino acid sequences based on the sequences of a plasmid pHGE 1221, which was positive in immunoscreening and contained an ORF encoding the proposed P44, were analyzed with DNASTAR computer software (DNASTAR Inc., 1228 South Park Street, Madison.). Several motifs with high antigenic index and probability of surface exposure were found in NH2-terminal portion. Therefore, the primers were designed to amplify the DNA sequence encoding for a 219-amino acid polypeptide from $NH_2$-terminus including 8 amino acid residues of signal peptide, and were prepared by BioServe (Laurel, Md.). The 5' oligonucleotide primer consists. of the DNA sequence coding for the $NH_2$-terminal region of the HGE agent P44 and the NcoI restriction sites (underlined) [5'-CG CCATGGCTGGGAGTGATGTCA-3'] and the 3' oligonucleotide primers consists of the DNA sequence coding for the amino acids from No. 243 to 247 with the addition of a stop codon (TAG, boldface) and a EcoRi restriction site (underlined) [5'-GC GAATTCTACGCACTACCATTACTCA-3') (FIG. 1). PCR amplification was carried out with a Perkin-Elmer Cetus DNA Thermal Cycler (Model 480) by using standard procedures. The 657-bp amplified product containing approximately half of the P44 gene was digested with NcoI and EcoRI, and ligated into dephosphorylated NcoI- and EcoRI-digested pET30a expression vector (Novagen, Inc., Madison, Wis.). The recombinant plasmid was designated as pEP44. E. coli NovaBlue strain (Novagen, Inc.) was transformed with recombinant pET30a. A plasmid preparation of pEP44 from transformed NovaBlue was then used to transform E. coli BL21(DE3)pLysS. The purification of rP44 protein was performed by using the His-Bind Buffer Kit (Novagen, Inc.) according to the manufacturer's instruction. The expressed partial recombinant P44 antigenic polypeptide (rP44) purified by affinity chromatography was 35 kDa in SDS-PAGE. It was a fusion polypeptide in which a 44-amino acid sequence including the His tag peptide derived from pET30a expression vector was located at the $NH_2$-terminus.

Example 3

Detecting HGE Infection with the rP44 Polypetide
A. Western Immunoblot Analysis

The affinity-purified rP44 polypeptide and purified HGE organisms were used for Western immunoblot analysis of patient sera. All HGE patient sera No. 2, 3, 4, 6, 11, 13, 21 and 22 were collected in the patients from Westchester County Medical Center in New York State. The diagnosis was confirmed by using PCR, IFA testing and culture islation. Patient sera No. 21-1, -2, -3, -4 and -5 were collected at different stages of illness (Jul. 25, 1995-first acute stage, Aug. 24, 1995-convalescent stage, Oct. 5, 1995, Jun. 13, 1996, and Jul. 17, 1997-second acute stage) from a patient suspected of having re-infection with the HGE agent.

Purified HGE agent and rP44 polypeptide separated by 10% PAGE were transferred to a nitrocellulose sheet, then immersed in TBS buffer (150 mM NaCl, 50 mM Tris-HCI [pH 7.4]) containing 0.05% Tween 20 (T-TBS) and 5% milk at 4° C. overnight to saturate protein-binding site. The nitrocellulose membrane was incubated with the primary mouse, human or horse sera at a 1:1,000 dilution and then with peroxidase-conjugated affinity purified anti-human, anti-horse or anti-mouse immunoglobulin G (Kirkegaard &

Perry Laboratories, Inc., Gaithersburg, Md.) at a 1:1,000 or 1:2,000 dilution. The peroxidase-positive bands were detected by immersing the sheet in a developing solution (70 mM sodium acetate, pH 6.2) containing 0.005% diaminobenzidine tetrahydrochloride (Nacalai Tesque, Inc., Kyoto, Japan) and 0.03% $H_2O_2$ at room temperature for 5 min. The enzyme reaction was terminated by washing the sheet in 0.1 M $H_2SO_4$.

Horse anti-HGE serum and eleven sera from the HGE patients specifically recognized the rP44 polypeptide. All these patients were confirmed to have HGE by PCR and/or culture isolation previously. Five sera collected over 2 year period at different stages of illness from a patient (No. 21) reacted with rP44. This patient was suspected of having re-infection with HOE agent, since IFA titer at 8 days before 21-5 serum collection date was 1:40. The result indicates that regardless of stages of infection or reinfection P44 is the major antigen recognized by the patient sera. The horse anti-*E. equi* serum strongly reacted with both native 44-kDa protein in whole cell organisms and rP44 polypeptide. Human anti-*E. chaffeensis* and rabbit anti-*B. burgdorferi* did not recognize rP44. This indicates that rP44 polypeptide can be used as a testing antigen to differentiate infection with HGE agent from infection with *E. chaffeensis* or *B. burgdorferi*.

B. Dot Immunoblot Assay

The affinity-purified rP44 polypeptide in TBS was blotted onto a nitrocellulose membrane (Schleicher & Schuell, Keene, N H), and then immersed T-TBS containing 5% milk at room temperature for 30 min, air dried, and stored at –20° C. until required. Based on the results of quantitative analysis, 0.5 ug per dot of rP44 was used in the immunoassay to assay the clinical specimens. For immunoassay, sera to be tested were diluted at 1:1,000 in T-TBS containing 5% milk and incubated with the antigen dots for 1 h at room temperature After being washed three times with T-TBS, the nitrocellulose sheets were incubated with peroxidase-conjugated affinity-purified anti-human IgG (Kirkegaard & Perry) at 1:2,000 dilution. The peroxidase-positive bands were detected by immersing the sheet in a developing solution as described in the Western immunoblot section. The color density was measured using background correction of ImageQuant program Molecular Dynamics, Sunnyvale, Calif.).

To determine the optimal amount of antigen of per dot and dilution of patient sera for dot blot immunoassay, nitrocellulose membrane strips, each having eight dots containing a different amount of purified rP44 antigen, were incubated with five different sera with IFA titers in a range from 1: 2,560 to <1: 20. There was a positive correlation between color densities of dot reactions and IFA titers when >50 ng of recombinant antigen was used per dot. No reaction was detected using negative control sera (IFA titer <1: 20). Since the difference of color density among sera with different IFA titers was quite distinct, and the color density progressively increased (especially at antigen amounts of 0.25 ug to 1 ug per dot), 0.5 ug per dot was used in the following assays. This amount of protein can distinguish both high and low titers.

A total of 25 clinical patient sera with different IFA titers (from 1:2,560 to <1: 20) were examined by dot blot immunoassay using 0.5 ug per dot of affinity-purified rP44. As shown in FIG. 6A, the color density of the each dot is highly correlated with the IFA titer. In five tested sera with an IFA titer <1: 20, the color density of one dot can be clearly distinguished from other negative sera by the naked eye. This sera was collected at acute phase from the patient No. 3 who was nested PCR and culture isolation positive for the HGE agent. This patient developed a convalescent IFA titer of 1: 640. The remaining four <1: 20 sera were derived from patients who were negative by convalescent serum IFA, PCR, or isolation. These results indicate that the dot immunoassay using rP44 protein provides a simpler serodiagnosis of HGE infection than the IFA test.

Example 4

Oligopeptides Specific to the P44 Protein, the P44-2 Protein, the P44-15 Protein, the P44-18 Protein, and the P44-19 Protein Synthetic oligopeptides specific to each Group 44 Protein were prepared. Such oligopeptides were identified, by using DNASTAR program (DNASTAR Inc., Madison, Wis.) and selected from the hypervariable region of the P44 protein, the P44-2 protein, the P44-15 protein and the P44-18 protein, and the P44-19 protein. Two oligopeptides with sequences of GHSSGVTQNPKLFST and KNQKSSDTDT-GVEKA were synthesized (Alpha Diagnostic, San Antonio, Tex.) and named Pep2 and Pep18, respectively. Pep2 and Pep28 were conjugated to keyhole limpet hemocyanin (KLH) and and the resulting KLH-conjugated oligopeptide Pep2 and Pep18 were used as antigens in a dot blot assay. The assay was carried out as described above in example 3. Convalescent sera tested were from two patients (no. 7, and no. 11) with clinical signs of HGE was confirmed by IFA and PCR. The results showed that oligopeptides are useful for detecting antibodies to the HGE causative agent in serum from patients afflicted with HGE.

Example 5

Anti-rP44 Polyclonal Antiserum

Hyperimmune anti-rP44 polyclonal antiserum was generated by intraperitoneal immunization of BALB/c male mice (6 weeks old) with rP44 affinity-purified as described above. Primary immunization of each animal was with 15 ug of purified rP44 in Freund's complete adjuvant. Two boosts of 10 ug each of rP44 in Freund's incomplete adjuvant followed at day 14 and 28. Hyperimmune serum was obtained 14 days after last boost The mouse antiserum specific to rP44 was used in a western immunoblot analysis. The antiserum strongly reacted with 44- and 42-kDa proteins in all isolates tested, and recognized a 27-kDa protein in No. 2 and 6 isolates, and a 1 5-kDa protein in No.2, 3, 6 and USG isolates.

Example 6

Antisera to KLH-coniugated Oligopeptide Pep2 and Pep18

Antisera against the KLH-conjugated oligopeptide Pep2 and Pep18 were generated by immunization of a rabbit and a mouse with keyhole limpet hemacyanin KLH) (PIERCE, Rockford, Ill.)-conjugated synthetic oligopeptide Pep2 and Pep18, respectively.

The resulting sera was used in a Western immunoblot analysis of the HGE agent lysate as described in example 3. The mouse anti-recombinant rP44 polypeptide anti-serum was used as a positive control. For double IFA staining, a lissamine rhodamine (LR)-labeled goat anti-rabbit IgG and fluorescein isothiocyanate (FITC)-labeled goat anti-mouse IgG (Jackson ImmunoResearch Laboratories, Inc., West Grove, Pa.) were used as secondary antibodies. The rabbit anti-Pep2 and the mouse anti-Pep18 sera reacted with a single band of 44 kDa and 43 kDa, respectively in the HGE agent lysate, respectively.

In host cells the HGE agent resides in membrane-bound inclusions that appear as clusters of organisms like mulberries, therefore, are called morulae. The morulae are considered as microcolonies derived from a single organism. Six morulae in an HL-60 cell which reacted with the mouse anti-rP44 serum were also recognized by the rabbit anti-Pep2 serum. All organisms were doublelabeled in 100 infected cells scored in three independent labeling experiments. This means a p44-2 gene is probably expressed in all of the HGE agent organisms cultivated in HL-60 cells. With a mouse anti-Pep18 serum even at low (1:5) dilution, the immunofluorescence labeling of organisms or morulae was extremely weak.

What is claimed is:

1. An isolated outer membrane protein of the human granulocytic ehrlichiosis causative agent, said protein comprising:
   a) a hypervariable region of about 94 amino acids, wherein said hypervariable region has an isoelectric point of from about 7.1 to about 9.2 and an Mr of from about 8.5 kDa to about 11 kDa;
   b) a first conserved region of about 52 amino acids linked directly or through a linker of from 1 to about 10 amino acids to the N-terminus of the hypervariable region;
   c) a second conserved region of about 56 amino acids linked directly or through a linker of from 1 to about 10 amino acids to the C teminus of said hypervariable region;
   wherein said hypervariable region has a hydrophilicity index of from about 0.45 to 0.95, an antigenic index of from about 0.65 to 1.5, and a surface probability index of from about 1.0 to 1.55.

2. The isolated protein of claim 1 wherein said isolated protein is immunoreactive with antiserum from patients with human granulocytic ehrlichiosis.

3. The isolated protein of claim 1 wherein said hypervariable region comprises:
   a) a first semiconserved region near the amino terminus thereof, said first semiconserved region comprising the sequence X1-X2-Lys-X3-Cys; wherein X1 is Asp or Gly, X2 is Gly or Lys, and X3 is Val or Ile;
   b) a second semiconserved region at the carboxy terminus thereof, said second second semiconserved region comprising the sequence Asn-Ala-X1-X2-X3-Ala-X4-X5-Leu-X6-X7; wherein X1 is Asn, Thr, Lys, or Glu, X2 is Ala or Lys, X3 is Met or Val; X4 is Lys, Gly, or Thr; X5 is Asp or Glu; X6 is Val or Thr, and X7 is Gln or Lys; and
   c) a third semiconserved region between the first and second semiconserved region, said third semiconserved region comprising the sequence Lys-X1-Trp-Pro-Thr-X2; wherein X1 is Asn or His and X2 is Gly, Thr, or Ser.

4. The isolated protein of claim 1
wherein said first conserved region has an amino acid sequence which is at least 95% identical to the amino acid sequence of the first conserved region of a protein selected from the group consisting of: the P44 protein, the P44-2 protein, the P44-12 protein, the P44-15 protein, the P44-18 protein, and the P44-19 protein, and
wherein said second conserved region has an amino acid sequence which is at least 95% identical to the amino acid sequence of the second conserved region of a protein selected from the group consisting of: the P44 protein, the P44-2 protein, the P44-12 protein, the P44-15 protein, the P44-18 protein, and the P44-19 protein.

5. An isolated outer membrane protein of the causative agent to human granulocytic ehrlichiosis, wherein said protein is selected from the group consisting of the P44 protein or a variant thereof; the P44-2 protein or a variant thereof; the P44-12 protein or a variant thereof; the P44-15 protein or a variant thereof, [a] the P44-18 protein or a variant thereof; and the P44-19 protein or a variant thereof.

6. The isolated protein of claim 5 wherein said protein comprises an amino acid sequence which is at least 90% identical to an amino acid sequence selected from the group consisting of the amino acid sequence SEQ ID NO:2, shown in FIG. 1; the amino acid sequence, SEQ ID NO: 4, shown in FIG. 2; the amino acid sequence, SEQ ID NO:6, shown in FIG. 3; the amino acid sequence, SEQ ID NO:8, shown in FIG. 4; the amino acid sequence, SEQ ID NO:10 shown in FIG. 5; and the amino acid sequence, SEQ ID NO:12, shown in FIG. 6.

7. The isolated protein of claim 6 wherein said protein is a mature protein and the amino acid sequence lacks the signal sequence.

8. An isolated polypeptide for producing antibodies immunospecific for a Group 44 protein, said polypeptide comprising a sequence which is at least 98% identical to an amino acid sequence selected from the group consisting of the amino acid sequence, SEQ ID NO:2, shown in FIG. 1; the amino acid sequence, SEQ ID NO: 4, shown in FIG. 2, the amino acid sequence, SEQ ID NO:6, shown in FIG. 3; the amino acid sequence, SEQ ID NO:8, shown in FIG. 4; the amino acid sequence, SEQ ID NO:10 shown in FIG. 5; and the amino acid sequence, SEQ ID NO:12, shown in FIG. 6.

9. An isolated polypeptide for producing antibodies immunospecific for a Group 44 protein, wherein said isolated polypeptide is 250 amino acids in length or less and comprises a sequence which is identical to the sequence of the hypervariable region of the P44 protein, the P44-2 protein, the P44-12 protein, the P44-15 protein, the P44-18 protein, or the P44-19 protein.

10. An isolated polypeptide for producing antibodies immunospecific for a Group 44 protein, wherein said polypeptide comprises amino acid 30 through amino acid 248 of the P44 protein or amino acid 38 through amino acid 248 of the P44 protein.

11. An isolated polypeptide for producing antibodies immunospecific for a Group 44 protein, wherein said polypeptide is 14 to 16 amino acids in length and comprises from 14 to 16 consecutive amino acids within LSNGSAEAAHKYLSK, SEQ ID NO: 19,
GHSSGVTQNPKLFST, SEQ ID NO: 20,
GKKSGDNGSLADYTD, SEQ ID NO: 21;
PLYSDETHTKGASEGR, SEQ ID NO: 22;
KNQKSSDTDTGVEKA, SEQ ID NO:23, or
TGSNKYGTGTNSGELT, SEQ ID NO: 24.

* * * * *

SEQUENCE LISTING

<160> NUMBER OF SEQ ID NOS: 44

<210> SEQ ID NO 1
<211> LENGTH: 1242
<212> TYPE: DNA
<213> ORGANISM: P44
<220> FEATURE:
<221> NAME/KEY: CDS
<222> LOCATION: (1)..(1242)

<400> SEQUENCE: 1

```
atg ttc tca ttt tct tta aaa ggc aga cct tcc ttt ttc gaa ata gcc      48
Met Phe Ser Phe Ser Leu Lys Gly Arg Pro Ser Phe Phe Glu Ile Ala
 1               5                  10                  15 ttt tct tta gga agc gta atg atg tct atg gct ata gtc atg gct ggg      96
Phe Ser Leu Gly Ser Val Met Met Ser Met Ala Ile Val Met Ala Gly
            20                  25                  30 agt gat gtc agg gct cat gat gac gtt agc gct ttg gag act ggt ggt     144
Ser Asp Val Arg Ala His Asp Asp Val Ser Ala Leu Glu Thr Gly Gly
        35                  40                  45 gcg gga tat ttc tat gtt ggt ttg gat tac agt cca gcg ttt agc aag     192
Ala Gly Tyr Phe Tyr Val Gly Leu Asp Tyr Ser Pro Ala Phe Ser Lys
    50                  55                  60 ata aga gat ttt agt ata agg gag agt aac gga gag act aag gca gta     240
Ile Arg Asp Phe Ser Ile Arg Glu Ser Asn Gly Glu Thr Lys Ala Val
65                  70                  75                  80 tat cca tac tta aag gat gga aag agt gta aag cta gag tca cac aag     288
Tyr Pro Tyr Leu Lys Asp Gly Lys Ser Val Lys Leu Glu Ser His Lys
                85                  90                  95 ttt gac tgg aac aca cct gat cct cgg att ggg ttt aag gac aac atg     336
Phe Asp Trp Asn Thr Pro Asp Pro Arg Ile Gly Phe Lys Asp Asn Met
            100                 105                 110 ctt gta gct atg gaa ggc agt gtt ggg tac cct att ggt ggt gcc agg     384
Leu Val Ala Met Glu Gly Ser Val Gly Tyr Pro Ile Gly Gly Ala Arg
        115                 120                 125 gtt gag ctt gag att ggt tac gag cgt ttc aag act aag ggt att aga     432
Val Glu Leu Glu Ile Gly Tyr Glu Arg Phe Lys Thr Lys Gly Ile Arg
    130                 135                 140 gat agt ggt agt aag gaa gat gaa gct gat aca gta tat cta cta gct     480
Asp Ser Gly Ser Lys Glu Asp Glu Ala Asp Thr Val Tyr Leu Leu Ala
145                 150                 155                 160 aag gag tta gct tat gat gtt gtt act ggg cag act gat aac ctt gct     528
Lys Glu Leu Ala Tyr Asp Val Val Thr Gly Gln Thr Asp Asn Leu Ala
                165                 170                 175 gct gct ctt gcc aaa acc tcc ggt aag gac atc gtt cag ttt gct aag     576
Ala Ala Leu Ala Lys Thr Ser Gly Lys Asp Ile Val Gln Phe Ala Lys
            180                 185                 190 gcg gtg gag atc tct tac cct agt atc gat ggg aag gtt tgt agt gga     624
Ala Val Glu Ile Ser Tyr Pro Ser Ile Asp Gly Lys Val Cys Ser Gly
        195                 200                 205 aag cat gcg gcg ctt gca gca aac acg aac gcg gag aaa aag tac gcg     672
```

```
                                                                                      -continued Lys His Ala Ala Leu Ala Ala Asn Thr Asn Ala Glu Lys Lys Tyr Ala
    210                 215                 220 gtt gag cct gcg aac ggc gga aca gac ggg agc acg tcg cag tgt agt                 720
Val Glu Pro Ala Asn Gly Gly Thr Asp Gly Ser Thr Ser Gln Cys Ser
225                 230                 235                 240 ggt ttg agt aat ggt agt gcg gag gct gct cat aaa tat ttg agt aag                 768
Gly Leu Ser Asn Gly Ser Ala Glu Ala Ala His Lys Tyr Leu Ser Lys
                245                 250                 255 ttt gta agt ctt acg gga gtg gtt gaa ggg aaa aac tgg cct act ggt                 816
Phe Val Ser Leu Thr Gly Val Val Glu Gly Lys Asn Trp Pro Thr Gly
            260                 265                 270 aga tcg agt aac aac agc aat agc att gta gtt gga gca cct aat agt                 864
Arg Ser Ser Asn Asn Ser Asn Ser Ile Val Val Gly Ala Pro Asn Ser
        275                 280                 285 aac gca aac gcg atg gcc aaa gat cta gta aag gaa cta aca cca gag                 912
Asn Ala Asn Ala Met Ala Lys Asp Leu Val Lys Glu Leu Thr Pro Glu
    290                 295                 300 gag aaa acc ata gtt gcc ggg tta cta gct aaa act att gaa ggg ggt                 960
Glu Lys Thr Ile Val Ala Gly Leu Leu Ala Lys Thr Ile Glu Gly Gly
305                 310                 315                 320 gag gtt gta gaa att agg gcg gtt tct tct act tct gta atg gtc aat                1008
Glu Val Val Glu Ile Arg Ala Val Ser Ser Thr Ser Val Met Val Asn
                325                 330                 335 gct tgt tat gat ctt ctt agt gaa ggt tta ggt gtt gtt cct tat gct                1056
Ala Cys Tyr Asp Leu Leu Ser Glu Gly Leu Gly Val Val Pro Tyr Ala
            340                 345                 350 tgt gtt ggt tta ggt ggt aac ttc gta ggt gtt gtt gat ggg cat atc                1104
Cys Val Gly Leu Gly Gly Asn Phe Val Gly Val Val Asp Gly His Ile
        355                 360                 365 act cct aag ctt gct tat agg tta aag gct ggc ttg agt tat cag ctc                1152
Thr Pro Lys Leu Ala Tyr Arg Leu Lys Ala Gly Leu Ser Tyr Gln Leu
    370                 375                 380 tct cct gaa atc tcc gct ttt gcg ggt gga ttc tac cat cgt gtt gtg                1200
Ser Pro Glu Ile Ser Ala Phe Ala Gly Gly Phe Tyr His Arg Val Val
385                 390                 395                 400 gga gat ggc gtt tat gat gat ctg ccg gag cct atg caa taa                        1242
Gly Asp Gly Val Tyr Asp Asp Leu Pro Glu Pro Met Gln
                405                 410

<210> SEQ ID NO 2
<211> LENGTH: 413
<212> TYPE: PRT
<213> ORGANISM: P44

<400> SEQUENCE: 2

Met Phe Ser Phe Ser Leu Lys Gly Arg Pro Ser Phe Phe Glu Ile Ala
1               5                   10                  15

Phe Ser Leu Gly Ser Val Met Met Ser Met Ala Ile Val Met Ala Gly
                20                  25                  30

Ser Asp Val Arg Ala His Asp Val Ser Ala Leu Glu Thr Gly Gly
            35                  40                  45

Ala Gly Tyr Phe Tyr Val Gly Leu Asp Tyr Ser Pro Ala Phe Ser Lys
        50                  55                  60

Ile Arg Asp Phe Ser Ile Arg Glu Ser Asn Gly Glu Thr Lys Ala Val
65                  70                  75                  80

Tyr Pro Tyr Leu Lys Asp Gly Lys Ser Val Lys Leu Glu Ser His Lys
                85                  90                  95

Phe Asp Trp Asn Thr Pro Asp Pro Arg Ile Gly Phe Lys Asp Asn Met
                100                 105                 110
```

```
Leu Val Ala Met Glu Gly Ser Val Gly Tyr Pro Ile Gly Gly Ala Arg
        115                 120                 125
Val Glu Leu Glu Ile Gly Tyr Glu Arg Phe Lys Thr Lys Gly Ile Arg
    130                 135                 140
Asp Ser Gly Ser Lys Glu Asp Glu Ala Asp Thr Val Tyr Leu Leu Ala
145                 150                 155                 160
Lys Glu Leu Ala Tyr Asp Val Val Thr Gly Gln Thr Asp Asn Leu Ala
                165                 170                 175
Ala Ala Leu Ala Lys Thr Ser Gly Lys Asp Ile Val Gln Phe Ala Lys
            180                 185                 190
Ala Val Glu Ile Ser Tyr Pro Ser Ile Asp Gly Lys Val Cys Ser Gly
        195                 200                 205
Lys His Ala Ala Leu Ala Ala Asn Thr Asn Ala Glu Lys Lys Tyr Ala
    210                 215                 220
Val Glu Pro Ala Asn Gly Gly Thr Asp Gly Ser Thr Ser Gln Cys Ser
225                 230                 235                 240
Gly Leu Ser Asn Gly Ser Ala Glu Ala Ala His Lys Tyr Leu Ser Lys
                245                 250                 255
Phe Val Ser Leu Thr Gly Val Val Glu Gly Lys Asn Trp Pro Thr Gly
            260                 265                 270
Arg Ser Ser Asn Asn Ser Asn Ser Ile Val Val Gly Ala Pro Asn Ser
        275                 280                 285
Asn Ala Asn Ala Met Ala Lys Asp Leu Val Lys Glu Leu Thr Pro Glu
    290                 295                 300
Glu Lys Thr Ile Val Ala Gly Leu Leu Ala Lys Thr Ile Glu Gly Gly
305                 310                 315                 320
Glu Val Val Glu Ile Arg Ala Val Ser Ser Thr Ser Val Met Val Asn
                325                 330                 335
Ala Cys Tyr Asp Leu Leu Ser Glu Gly Leu Gly Val Val Pro Tyr Ala
            340                 345                 350
Cys Val Gly Leu Gly Gly Asn Phe Val Gly Val Asp Gly His Ile
        355                 360                 365
Thr Pro Lys Leu Ala Tyr Arg Leu Lys Ala Gly Leu Ser Tyr Gln Leu
    370                 375                 380
Ser Pro Glu Ile Ser Ala Phe Ala Gly Gly Phe Tyr His Arg Val Val
385                 390                 395                 400
Gly Asp Gly Val Tyr Asp Asp Leu Pro Glu Pro Met Gln
                405                 410

<210> SEQ ID NO 3
<211> LENGTH: 1278
<212> TYPE: DNA
<213> ORGANISM: P44-2
<220> FEATURE:
<221> NAME/KEY: CDS
<222> LOCATION: (1)..(1278)

<400> SEQUENCE: 3 atg atg tca atg gct ata gtc atg gct ggg aat gat gtc agg gct cat    48
Met Met Ser Met Ala Ile Val Met Ala Gly Asn Asp Val Arg Ala His
  1               5                  10                  15 gat gac gtt agc gct ttg gag aat ggt ggt gcg gga tat ttc tat gtt    96
Asp Asp Val Ser Ala Leu Glu Asn Gly Gly Ala Gly Tyr Phe Tyr Val
                 20                  25                  30 ggt ttg gat tac agt cca gcg ttt agc aag ata aga gat ttt agt ata   144
Gly Leu Asp Tyr Ser Pro Ala Phe Ser Lys Ile Arg Asp Phe Ser Ile
```

```
                   35                    40                       45
agg gag agt aac gga gag aca aag gca gta tat cca tac tta aag gat     192
Arg Glu Ser Asn Gly Glu Thr Lys Ala Val Tyr Pro Tyr Leu Lys Asp
         50                   55                      60 gga aag agt gta aag ctt gag tcg cac aag ttt gac tgg aac aca cct     240
Gly Lys Ser Val Lys Leu Glu Ser His Lys Phe Asp Trp Asn Thr Pro
 65                   70                  75                  80 gat cct cgg att ggg ttt aag gac aac atg ctt gta gct atg gaa ggc     288
Asp Pro Arg Ile Gly Phe Lys Asp Asn Met Leu Val Ala Met Glu Gly
                     85                  90                  95 agt gtt ggt tat ggt att ggt ggt gcc agg gtt gag ctt gag att ggt     336
Ser Val Gly Tyr Gly Ile Gly Gly Ala Arg Val Glu Leu Glu Ile Gly
                    100                 105                 110 tac gag cgc ttc aag acc aag ggt att aga gat agt ggt agt aag gaa     384
Tyr Glu Arg Phe Lys Thr Lys Gly Ile Arg Asp Ser Gly Ser Lys Glu
             115                 120                 125 gat gaa gct gat aca gta tat cta cta gct aag gag tta gct tat gat     432
Asp Glu Ala Asp Thr Val Tyr Leu Leu Ala Lys Glu Leu Ala Tyr Asp
 130                 135                 140 gtt gtt act gga cag act gat aag ctt acc gct gct ctt gcc aag acc     480
Val Val Thr Gly Gln Thr Asp Lys Leu Thr Ala Ala Leu Ala Lys Thr
145                 150                 155                 160 tcc ggt aaa gat atc gtt cag ttt gcg aat gct gtg aaa att tct agc     528
Ser Gly Lys Asp Ile Val Gln Phe Ala Asn Ala Val Lys Ile Ser Ser
                    165                 170                 175 tct gcc atc gat ggg aag gtt tgt act ggt agc cat gct gac cta gcg     576
Ser Ala Ile Asp Gly Lys Val Cys Thr Gly Ser His Ala Asp Leu Ala
                180                 185                 190 cct ggt acg aat gcg ggg aaa aag ttc gtt gtg aac ccg gaa gcc agc     624
Pro Gly Thr Asn Ala Gly Lys Lys Phe Val Val Asn Pro Glu Ala Ser
            195                 200                 205 ggg agt act gat ggg gat acg tca cag tgt agt ggt tta ggg cat agt     672
Gly Ser Thr Asp Gly Asp Thr Ser Gln Cys Ser Gly Leu Gly His Ser
        210                 215                 220 agt ggt gtt aca cag aat ccg aag tta ttt agt act ttt gtg gac act     720
Ser Gly Val Thr Gln Asn Pro Lys Leu Phe Ser Thr Phe Val Asp Thr
225                 230                 235                 240 gtg aag att gct gag gat aaa aac tgg ccg acg ggc agg gca aaa tcg     768
Val Lys Ile Ala Glu Asp Lys Asn Trp Pro Thr Gly Arg Ala Lys Ser
                    245                 250                 255 aac aca tca ctg aag acg ggt gat act aat agt aac gcc aaa gcc gtg     816
Asn Thr Ser Leu Lys Thr Gly Asp Thr Asn Ser Asn Ala Lys Ala Val
                260                 265                 270 gct aca gac cta gta cag gag cta acc cct gaa gaa aaa acc ata gta     864
Ala Thr Asp Leu Val Gln Glu Leu Thr Pro Glu Glu Lys Thr Ile Val
            275                 280                 285 gca ggg tta cta gct aag act att gaa ggg ggt gaa gtt gtt gag atc     912
Ala Gly Leu Leu Ala Lys Thr Ile Glu Gly Gly Glu Val Val Glu Ile
        290                 295                 300 agg gcg gtt tct tct act tcc gta atg gtc aat gct tgt tat gat ctt     960
Arg Ala Val Ser Ser Thr Ser Val Met Val Asn Ala Cys Tyr Asp Leu
305                 310                 315                 320 ctt agt gaa ggt tta tgt gtt gtt cct tat gct tgt gtt ggt ctt ggc    1008
Leu Ser Glu Gly Leu Cys Val Val Pro Tyr Ala Cys Val Gly Leu Gly
                    325                 330                 335 ggt aac ttc gtg ggc gtg gtt gat ggc cat atc act cct aag ctt gct    1056
Gly Asn Phe Val Gly Val Val Asp Gly His Ile Thr Pro Lys Leu Ala
                340                 345                 350 tat aga tta aag gct ggg ttg agt tat cag ctc tct cct gta atc tcc    1104
```

```
                Tyr Arg Leu Lys Ala Gly Leu Ser Tyr Gln Leu Ser Pro Val Ile Ser
                        355                 360                 365 gct ttt gcg ggt gga ttc tac cat cgc gtt gtg gga gat ggc gtt tat        1152
Ala Phe Ala Gly Gly Phe Tyr His Arg Val Val Gly Asp Gly Val Tyr
370                 375                 380 gat gat ctg ccg gct caa cgt ctt gta gat gat act agt ccg gcg ggc        1200
Asp Asp Leu Pro Ala Gln Arg Leu Val Asp Asp Thr Ser Pro Ala Gly
385                 390                 395                 400 cgt act aag gat act gct att gct aac ttc tcc atg gct tat gtc ggt        1248
Arg Thr Lys Asp Thr Ala Ile Ala Asn Phe Ser Met Ala Tyr Val Gly
                405                 410                 415 ggg gaa ttt ggt gtt agg ttc gct ttt taa                                1278
Gly Glu Phe Gly Val Arg Phe Ala Phe
                420                 425

<210> SEQ ID NO 4
<211> LENGTH: 425
<212> TYPE: PRT
<213> ORGANISM: P44-2

<400> SEQUENCE: 4

Met Met Ser Met Ala Ile Val Met Ala Gly Asn Asp Val Arg Ala His
1               5                   10                  15

Asp Asp Val Ser Ala Leu Glu Asn Gly Gly Ala Gly Tyr Phe Tyr Val
                20                  25                  30

Gly Leu Asp Tyr Ser Pro Ala Phe Ser Lys Ile Arg Asp Phe Ser Ile
            35                  40                  45

Arg Glu Ser Asn Gly Glu Thr Lys Ala Val Tyr Pro Tyr Leu Lys Asp
        50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
                100                 105                 110

Tyr Glu Arg Phe Lys Thr Lys Gly Ile Arg Asp Ser Gly Ser Lys Glu
            115                 120                 125

Asp Glu Ala Asp Thr Val Tyr Leu Leu Ala Lys Glu Leu Ala Tyr Asp
        130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Asn Ala Val Lys Ile Ser Ser
                165                 170                 175

Ser Ala Ile Asp Gly Lys Val Cys Thr Gly Ser His Ala Asp Leu Ala
                180                 185                 190

Pro Gly Thr Asn Ala Gly Lys Lys Phe Val Val Asn Pro Glu Ala Ser
            195                 200                 205

Gly Ser Thr Asp Gly Asp Thr Ser Gln Cys Ser Gly Leu Gly His Ser
        210                 215                 220

Ser Gly Val Thr Gln Asn Pro Lys Leu Phe Ser Thr Phe Val Asp Thr
225                 230                 235                 240

Val Lys Ile Ala Glu Asp Lys Asn Trp Pro Thr Gly Arg Ala Lys Ser
                245                 250                 255

Asn Thr Ser Leu Lys Thr Gly Asp Thr Asn Ser Asn Ala Lys Ala Val
                260                 265                 270

Ala Thr Asp Leu Val Gln Glu Leu Thr Pro Glu Glu Lys Thr Ile Val
```

```
                275                 280                      285
Ala Gly Leu Leu Ala Lys Thr Ile Glu Gly Gly Glu Val Val Glu Ile
        290                 295                 300

Arg Ala Val Ser Ser Thr Ser Val Met Val Asn Ala Cys Tyr Asp Leu
305                 310                 315                 320

Leu Ser Glu Gly Leu Cys Val Val Pro Tyr Ala Cys Val Gly Leu Gly
                325                 330                 335

Gly Asn Phe Val Gly Val Val Asp Gly His Ile Thr Pro Lys Leu Ala
                340                 345                 350

Tyr Arg Leu Lys Ala Gly Leu Ser Tyr Gln Leu Ser Pro Val Ile Ser
                355                 360                 365

Ala Phe Ala Gly Gly Phe Tyr His Arg Val Val Gly Asp Gly Val Tyr
        370                 375                 380

Asp Asp Leu Pro Ala Gln Arg Leu Val Asp Thr Ser Pro Ala Gly
385                 390                 395                 400

Arg Thr Lys Asp Thr Ala Ile Ala Asn Phe Ser Met Ala Tyr Val Gly
                405                 410                 415

Gly Glu Phe Gly Val Arg Phe Ala Phe
                420                 425

<210> SEQ ID NO 5
<211> LENGTH: 1176
<212> TYPE: DNA
<213> ORGANISM: P44-12
<220> FEATURE:
<221> NAME/KEY: CDS
<222> LOCATION: (1)..(1176)

<400> SEQUENCE: 5 atg atg tct atg gct ata gtc atg gct ggg aat gat gtc agg gct cat       48
Met Met Ser Met Ala Ile Val Met Ala Gly Asn Asp Val Arg Ala His
 1               5                  10                  15 gat gac gtt agc gct ttg gag act ggt ggt gcg gga tat ttc tat gtt       96
Asp Asp Val Ser Ala Leu Glu Thr Gly Gly Ala Gly Tyr Phe Tyr Val
                20                  25                  30 ggc ttg gat tac agt cca gcg ttt agc aag ata aga gat ttt agt ata      144
Gly Leu Asp Tyr Ser Pro Ala Phe Ser Lys Ile Arg Asp Phe Ser Ile
             35                  40                  45 agg gag agt aac gga gag act aag gca gta tat cca tac tta aag gat      192
Arg Glu Ser Asn Gly Glu Thr Lys Ala Val Tyr Pro Tyr Leu Lys Asp
     50                  55                  60 gga aag agt gta aag cta gag tca cac aag ttt gac tgg aac act cct      240
Gly Lys Ser Val Lys Leu Glu Ser His Lys Phe Asp Trp Asn Thr Pro
 65                  70                  75                  80 gat cct cgg att ggg ttt aag gac aac atg ctt gta gct atg gaa ggc      288
Asp Pro Arg Ile Gly Phe Lys Asp Asn Met Leu Val Ala Met Glu Gly
                 85                  90                  95 agt gtt ggt tat ggt att ggt ggt gcc agg gtt gag ctt gag att ggt      336
Ser Val Gly Tyr Gly Ile Gly Gly Ala Arg Val Glu Leu Glu Ile Gly
            100                 105                 110 tac gag cgc ttc aag acc aag ggt att aga gat agt ggt agt aag gaa      384
Tyr Glu Arg Phe Lys Thr Lys Gly Ile Arg Asp Ser Gly Ser Lys Glu
        115                 120                 125 gat gaa gct gat aca gta tat cta cta gct aag gag tta gct tat gat      432
Asp Glu Ala Asp Thr Val Tyr Leu Leu Ala Lys Glu Leu Ala Tyr Asp
    130                 135                 140 gtt gtt act ggg cag act gat aac ctt gct gct gct ctt gcc aag acc      480
Val Val Thr Gly Gln Thr Asp Asn Leu Ala Ala Ala Leu Ala Lys Thr
145                 150                 155                 160
```

```
tct ggt aaa gat att gtt cag ttt gct aag gcg gtt ggg gtt tct cat    528
Ser Gly Lys Asp Ile Val Gln Phe Ala Lys Ala Val Gly Val Ser His
            165                 170                 175 ccc ggt att gat aag aag gtt tgt gat ggg ggt cat gca cgg gga aaa    576
Pro Gly Ile Asp Lys Lys Val Cys Asp Gly Gly His Ala Arg Gly Lys
            180                 185                 190 aag agt gga gat aat ggc tcg ctg gcc gac tat acg gat ggt ggc gcg    624
Lys Ser Gly Asp Asn Gly Ser Leu Ala Asp Tyr Thr Asp Gly Gly Ala
            195                 200                 205 tca cag acg aat aag acg gct cag tgt agt ggt atg gga acc ggc aaa    672
Ser Gln Thr Asn Lys Thr Ala Gln Cys Ser Gly Met Gly Thr Gly Lys
            210                 215                 220 gcc ggc aag aga gga ttg ggc ttg act gag ttt gtt aac aaa aca aag    720
Ala Gly Lys Arg Gly Leu Gly Leu Thr Glu Phe Val Asn Lys Thr Lys
225                 230                 235                 240 gtt gga gaa ggt aag aat tgg cca acg ggg tac gtt aat gat ggc gac    768
Val Gly Glu Gly Lys Asn Trp Pro Thr Gly Tyr Val Asn Asp Gly Asp
            245                 250                 255 aac gtt aat gtg ctc ggc gat acg aat ggt aac gcc gaa gcc gta gct    816
Asn Val Asn Val Leu Gly Asp Thr Asn Gly Asn Ala Glu Ala Val Ala
            260                 265                 270 aaa gac cta gta cag gag cta acc cct gaa gaa aaa acc ata gta gca    864
Lys Asp Leu Val Gln Glu Leu Thr Pro Glu Glu Lys Thr Ile Val Ala
            275                 280                 285 ggg tta cta gct aag act att gaa ggg ggt gaa gtt gtt gag atc agg    912
Gly Leu Leu Ala Lys Thr Ile Glu Gly Gly Glu Val Val Glu Ile Arg
            290                 295                 300 gcg gtt tct tct act tcc gta atg gtc aat gct tgt tat gat ctt ctt    960
Ala Val Ser Ser Thr Ser Val Met Val Asn Ala Cys Tyr Asp Leu Leu
305                 310                 315                 320 agt gaa ggt tta ggt gtt gtt cct tat gct tgt gtt ggt ctt ggc ggt   1008
Ser Glu Gly Leu Gly Val Val Pro Tyr Ala Cys Val Gly Leu Gly Gly
            325                 330                 335 aac ttc gtg ggc gtg gtt gat ggc cat atc act cct aag ctt gct tat   1056
Asn Phe Val Gly Val Val Asp Gly His Ile Thr Pro Lys Leu Ala Tyr
            340                 345                 350 aga tta aag gct ggg ttg agt tat cag ctc tct cct gta atc tcc gct   1104
Arg Leu Lys Ala Gly Leu Ser Tyr Gln Leu Ser Pro Val Ile Ser Ala
            355                 360                 365 ttt gcg ggt gga ttc tac cat cgc gtt gtg gga gat ggc gtt tat gat   1152
Phe Ala Gly Gly Phe Tyr His Arg Val Val Gly Asp Gly Val Tyr Asp
            370                 375                 380 gat ctg ccg gct caa cta cct tga                                    1176
Asp Leu Pro Ala Gln Leu Pro
385                 390

<210> SEQ ID NO 6
<211> LENGTH: 391
<212> TYPE: PRT
<213> ORGANISM: P44-12

<400> SEQUENCE: 6

Met Met Ser Met Ala Ile Val Met Ala Gly Asn Asp Val Arg Ala His
  1               5                  10                  15

Asp Asp Val Ser Ala Leu Glu Thr Gly Gly Ala Gly Tyr Phe Tyr Val
                 20                  25                  30

Gly Leu Asp Tyr Ser Pro Ala Phe Ser Lys Ile Arg Asp Phe Ser Ile
             35                  40                  45

Arg Glu Ser Asn Gly Glu Thr Lys Ala Val Tyr Pro Tyr Leu Lys Asp
```

|   |   |   | 50  |   |   |   | 55  |   |   |   | 60  |   |
|---|---|---|-----|---|---|---|-----|---|---|---|-----|---|

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
            100                 105                 110

Tyr Glu Arg Phe Lys Thr Lys Gly Ile Arg Asp Ser Gly Ser Lys Glu
        115                 120                 125

Asp Glu Ala Asp Thr Val Tyr Leu Leu Ala Lys Glu Leu Ala Tyr Asp
    130                 135                 140

Val Val Thr Gly Gln Thr Asp Asn Leu Ala Ala Leu Ala Lys Thr
145                 150                 155                 160

Ser Gly Lys Asp Ile Val Gln Phe Ala Lys Ala Val Gly Val Ser His
                165                 170                 175

Pro Gly Ile Asp Lys Lys Val Cys Asp Gly His Ala Arg Gly Lys
                180                 185                 190

Lys Ser Gly Asp Asn Gly Ser Leu Ala Asp Tyr Thr Asp Gly Ala
            195                 200                 205

Ser Gln Thr Asn Lys Thr Ala Gln Cys Ser Gly Met Gly Thr Gly Lys
    210                 215                 220

Ala Gly Lys Arg Gly Leu Gly Leu Thr Glu Phe Val Asn Lys Thr Lys
225                 230                 235                 240

Val Gly Glu Gly Lys Asn Trp Pro Thr Gly Tyr Val Asn Asp Gly Asp
                245                 250                 255

Asn Val Asn Val Leu Gly Asp Thr Asn Gly Asn Ala Glu Ala Val Ala
            260                 265                 270

Lys Asp Leu Val Gln Glu Leu Thr Pro Glu Glu Lys Thr Ile Val Ala
        275                 280                 285

Gly Leu Leu Ala Lys Thr Ile Glu Gly Gly Glu Val Val Glu Ile Arg
    290                 295                 300

Ala Val Ser Ser Thr Ser Val Met Val Asn Ala Cys Tyr Asp Leu Leu
305                 310                 315                 320

Ser Glu Gly Leu Gly Val Val Pro Tyr Ala Cys Val Gly Leu Gly Gly
                325                 330                 335

Asn Phe Val Gly Val Asp Gly His Ile Thr Pro Lys Leu Ala Tyr
            340                 345                 350

Arg Leu Lys Ala Gly Leu Ser Tyr Gln Leu Ser Pro Val Ile Ser Ala
        355                 360                 365

Phe Ala Gly Gly Phe Tyr His Arg Val Val Gly Asp Gly Val Tyr Asp
    370                 375                 380

Asp Leu Pro Ala Gln Leu Pro
385                 390

<210> SEQ ID NO 7
<211> LENGTH: 837
<212> TYPE: DNA
<213> ORGANISM: P44-15
<220> FEATURE:
<221> NAME/KEY: CDS
<222> LOCATION: (1)..(837)

<400> SEQUENCE: 7

| ttt | acc | ttg | gaa | cca | tta | tca | ggg | aga | aga | aat | agg | aat | att | aag | agt | 48 |
|-----|-----|-----|-----|-----|-----|-----|-----|-----|-----|-----|-----|-----|-----|-----|-----|----|
| Phe | Thr | Leu | Glu | Pro | Leu | Ser | Gly | Arg | Arg | Asn | Arg | Asn | Ile | Lys | Ser |    |
| 1   |     |     |     | 5   |     |     |     |     | 10  |     |     |     |     | 15  |     |    |

```
cta ata agt tta tta ttg aga cca agg gta tta gag att agt ggt agt     96
Leu Ile Ser Leu Leu Leu Arg Pro Arg Val Leu Glu Ile Ser Gly Ser
        20                  25                  30 aag gaa gat gaa gct gat aca gta tat cta cta gct aag gag tta gct    144
Lys Glu Asp Glu Ala Asp Thr Val Tyr Leu Leu Ala Lys Glu Leu Ala
            35                  40                  45 tat gat gtt gtt act ggg cag act gat aac ctt gcc gct gct ctg gcc    192
Tyr Asp Val Val Thr Gly Gln Thr Asp Asn Leu Ala Ala Ala Leu Ala
 50                  55                  60 aaa acc tcc ggt aaa gac ttt gtc cag ttt gct aag gcg gtt ggg gtt    240
Lys Thr Ser Gly Lys Asp Phe Val Gln Phe Ala Lys Ala Val Gly Val
 65                  70                  75                  80 tct cat cct agt att gat ggg aag gtt tgt aag acg aag gcg gat agc    288
Ser His Pro Ser Ile Asp Gly Lys Val Cys Lys Thr Lys Ala Asp Ser
                    85                  90                  95 tcg aag aaa ttt ccg tta tat agt gac gaa acg cac acg aag ggg gca    336
Ser Lys Lys Phe Pro Leu Tyr Ser Asp Glu Thr His Thr Lys Gly Ala
                100                 105                 110 agt gag ggg aga acg tct ttg tgc ggt gac aat ggt agt tct acg ata    384
Ser Glu Gly Arg Thr Ser Leu Cys Gly Asp Asn Gly Ser Ser Thr Ile
            115                 120                 125 aca aac agt ggt gcg aat gta agt gaa act ggg cag gtt ttt agg gat    432
Thr Asn Ser Gly Ala Asn Val Ser Glu Thr Gly Gln Val Phe Arg Asp
130                 135                 140 ttt atc agg gca acg ctg aaa gag gat ggt agt aaa aac tgg cca act    480
Phe Ile Arg Ala Thr Leu Lys Glu Asp Gly Ser Lys Asn Trp Pro Thr
145                 150                 155                 160 tca agc ggc acg gga act cca aaa cct gtc acg aac gac aac gcc aaa    528
Ser Ser Gly Thr Gly Thr Pro Lys Pro Val Thr Asn Asp Asn Ala Lys
                165                 170                 175 gcc gta gct aaa gac cta gta cag gag cta acc cct gaa gaa aaa acc    576
Ala Val Ala Lys Asp Leu Val Gln Glu Leu Thr Pro Glu Glu Lys Thr
                180                 185                 190 ata gta gca ggg tta cta gct aaa act att gaa ggt ggt gag gtt att    624
Ile Val Ala Gly Leu Leu Ala Lys Thr Ile Glu Gly Gly Glu Val Ile
            195                 200                 205 gaa atc agg gcg gtt tct tct act tct gtg atg gtc aat gct tgt tat    672
Glu Ile Arg Ala Val Ser Ser Thr Ser Val Met Val Asn Ala Cys Tyr
210                 215                 220 gat ctt ctt agt gaa ggt tta ggt gtt gtc cct tat gct tgt gtt ggt    720
Asp Leu Leu Ser Glu Gly Leu Gly Val Val Pro Tyr Ala Cys Val Gly
225                 230                 235                 240 ctt gtg ggt aac ttc gta ggt gtt gtt gat ggg cat atc act cct aag    768
Leu Val Gly Asn Phe Val Gly Val Val Asp Gly His Ile Thr Pro Lys
                245                 250                 255 ctt gct tat aga tta aag gct ggc ttg agt tat cag ctc tct cct gta    816
Leu Ala Tyr Arg Leu Lys Ala Gly Leu Ser Tyr Gln Leu Ser Pro Val
                260                 265                 270 atc tct tct ttc tca gta tga                                         837
Ile Ser Ser Phe Ser Val
                275

<210> SEQ ID NO 8
<211> LENGTH: 278
<212> TYPE: PRT
<213> ORGANISM: P44-15

<400> SEQUENCE: 8

Phe Thr Leu Glu Pro Leu Ser Gly Arg Arg Asn Arg Asn Ile Lys Ser
 1               5                   10                  15
```

```
Leu Ile Ser Leu Leu Arg Pro Arg Val Leu Glu Ile Ser Gly Ser
         20                  25                  30

Lys Glu Asp Glu Ala Asp Thr Val Tyr Leu Leu Ala Lys Glu Leu Ala
         35                  40                  45

Tyr Asp Val Val Thr Gly Gln Thr Asp Asn Leu Ala Ala Leu Ala
 50                  55                  60

Lys Thr Ser Gly Lys Asp Phe Val Gln Phe Ala Lys Ala Val Gly Val
 65                  70                  75                  80

Ser His Pro Ser Ile Asp Gly Lys Val Cys Lys Thr Lys Ala Asp Ser
                 85                  90                  95

Ser Lys Lys Phe Pro Leu Tyr Ser Asp Glu Thr His Thr Lys Gly Ala
            100                 105                 110

Ser Glu Gly Arg Thr Ser Leu Cys Gly Asp Asn Gly Ser Ser Thr Ile
        115                 120                 125

Thr Asn Ser Gly Ala Asn Val Ser Glu Thr Gly Gln Val Phe Arg Asp
    130                 135                 140

Phe Ile Arg Ala Thr Leu Lys Glu Asp Gly Ser Lys Asn Trp Pro Thr
145                 150                 155                 160

Ser Ser Gly Thr Gly Thr Pro Lys Pro Val Thr Asn Asp Asn Ala Lys
                165                 170                 175

Ala Val Ala Lys Asp Leu Val Gln Glu Leu Thr Pro Glu Glu Lys Thr
            180                 185                 190

Ile Val Ala Gly Leu Leu Ala Lys Thr Ile Glu Gly Gly Glu Val Ile
        195                 200                 205

Glu Ile Arg Ala Val Ser Ser Thr Ser Val Met Val Asn Ala Cys Tyr
    210                 215                 220

Asp Leu Leu Ser Glu Gly Leu Gly Val Val Pro Tyr Ala Cys Val Gly
225                 230                 235                 240

Leu Val Gly Asn Phe Val Gly Val Val Asp Gly His Ile Thr Pro Lys
                245                 250                 255

Leu Ala Tyr Arg Leu Lys Ala Gly Leu Ser Tyr Gln Leu Ser Pro Val
            260                 265                 270

Ile Ser Ser Phe Ser Val
        275

<210> SEQ ID NO 9
<211> LENGTH: 759
<212> TYPE: DNA
<213> ORGANISM: P44-18
<220> FEATURE:
<221> NAME/KEY: CDS
<222> LOCATION: (1)..(759)

<400> SEQUENCE: 9 tct gcc gga gcc tat gca ata att ctt att att gaa aac aag acc aag    48
Ser Ala Gly Ala Tyr Ala Ile Ile Leu Ile Ile Glu Asn Lys Thr Lys
 1               5                  10                  15 ggt att aga gat agt ggt agt aag gaa gat gaa gct gat aca gta tat    96
Gly Ile Arg Asp Ser Gly Ser Lys Glu Asp Glu Ala Asp Thr Val Tyr
             20                  25                  30 cta cta gct aag gag tta gct tat gat gtt gtt act ggg cag act gat   144
Leu Leu Ala Lys Glu Leu Ala Tyr Asp Val Val Thr Gly Gln Thr Asp
         35                  40                  45 aac ctt gcc gct gct ctt gcc aaa acc tca ggt aag gac atc gtt cag   192
Asn Leu Ala Ala Ala Leu Ala Lys Thr Ser Gly Lys Asp Ile Val Gln
     50                  55                  60
```

-continued

```
ttt gct aag gcc gtg gag att tct aat tcc ggt att ggt aag aag gtg         240
Phe Ala Lys Ala Val Glu Ile Ser Asn Ser Gly Ile Gly Lys Lys Val
 65                  70                  75                  80 tgt gag aca aag cgg aag gat ggt gat act acg aac agg ttt gca aag         288
Cys Glu Thr Lys Arg Lys Asp Gly Asp Thr Thr Asn Arg Phe Ala Lys
                 85                  90                  95 tat ata gtt ggt gcg ggt gat agt agc aat gct ggt aca tca ttg tgt         336
Tyr Ile Val Gly Ala Gly Asp Ser Ser Asn Ala Gly Thr Ser Leu Cys
            100                 105                 110 ggt ggt aag aac caa aag agt tcg gac aca gac acc ggg gtg gag aag         384
Gly Gly Lys Asn Gln Lys Ser Ser Asp Thr Asp Thr Gly Val Glu Lys
        115                 120                 125 gct cag gct ctg cat gac ttt gtt tct aac aca ttg agt gat ggt act         432
Ala Gln Ala Leu His Asp Phe Val Ser Asn Thr Leu Ser Asp Gly Thr
130                 135                 140 aag aac tgg cct acg tcg agt gaa acg tct aaa tcg aat aac gac aac         480
Lys Asn Trp Pro Thr Ser Ser Glu Thr Ser Lys Ser Asn Asn Asp Asn
145                 150                 155                 160 gcc aaa gct gta gcg gga gac tta act aag aag ctc acc cct gaa gaa         528
Ala Lys Ala Val Ala Gly Asp Leu Thr Lys Lys Leu Thr Pro Glu Glu
                165                 170                 175 aaa acc ata gta gca ggg tta cta gct aag act att gaa ggt ggt gag         576
Lys Thr Ile Val Ala Gly Leu Leu Ala Lys Thr Ile Glu Gly Gly Glu
            180                 185                 190 gtt gtt gaa att agg gcg gtt tct tct act tct gtg atg gtt aat gct         624
Val Val Glu Ile Arg Ala Val Ser Ser Thr Ser Val Met Val Asn Ala
        195                 200                 205 tgt tat gat ctt ctt agt gaa ggt tta ggc gtt gtt cct tat gct tgt         672
Cys Tyr Asp Leu Leu Ser Glu Gly Leu Gly Val Val Pro Tyr Ala Cys
210                 215                 220 gtt ggt ctc ggt gga aac ttc gtt ggt gtt gtt gac gag tac agc aca         720
Val Gly Leu Gly Gly Asn Phe Val Gly Val Val Asp Glu Tyr Ser Thr
225                 230                 235                 240 atc cgt ccg tct tta acc cta tat gcc cgt aga aag taa                     759
Ile Arg Pro Ser Leu Thr Leu Tyr Ala Arg Arg Lys
                245                 250
```

<210> SEQ ID NO 10
<211> LENGTH: 252
<212> TYPE: PRT
<213> ORGANISM: P44-18

<400> SEQUENCE: 10

```
Ser Ala Gly Ala Tyr Ala Ile Ile Leu Ile Ile Glu Asn Lys Thr Lys
 1               5                  10                  15

Gly Ile Arg Asp Ser Gly Ser Lys Glu Asp Glu Ala Asp Thr Val Tyr
            20                  25                  30

Leu Leu Ala Lys Glu Leu Ala Tyr Asp Val Val Thr Gly Gln Thr Asp
        35                  40                  45

Asn Leu Ala Ala Leu Ala Lys Thr Ser Gly Lys Asp Ile Val Gln
    50                  55                  60

Phe Ala Lys Ala Val Glu Ile Ser Asn Ser Gly Ile Gly Lys Lys Val
 65                  70                  75                  80

Cys Glu Thr Lys Arg Lys Asp Gly Asp Thr Thr Asn Arg Phe Ala Lys
                 85                  90                  95

Tyr Ile Val Gly Ala Gly Asp Ser Ser Asn Ala Gly Thr Ser Leu Cys
            100                 105                 110

Gly Gly Lys Asn Gln Lys Ser Ser Asp Thr Asp Thr Gly Val Glu Lys
        115                 120                 125
```

```
Ala Gln Ala Leu His Asp Phe Val Ser Asn Thr Leu Ser Asp Gly Thr
    130                 135                 140
Lys Asn Trp Pro Thr Ser Ser Glu Thr Ser Lys Ser Asn Asn Asp Asn
145                 150                 155                 160
Ala Lys Ala Val Ala Gly Asp Leu Thr Lys Lys Leu Thr Pro Glu Glu
                165                 170                 175
Lys Thr Ile Val Ala Gly Leu Leu Ala Lys Thr Ile Glu Gly Gly Glu
                180                 185                 190
Val Val Glu Ile Arg Ala Val Ser Ser Thr Ser Val Met Val Asn Ala
            195                 200                 205
Cys Tyr Asp Leu Leu Ser Glu Gly Leu Gly Val Val Pro Tyr Ala Cys
    210                 215                 220
Val Gly Leu Gly Gly Asn Phe Val Gly Val Val Asp Glu Tyr Ser Thr
225                 230                 235                 240
Ile Arg Pro Ser Leu Thr Leu Tyr Ala Arg Arg Lys
                245                 250

<210> SEQ ID NO 11
<211> LENGTH: 492
<212> TYPE: DNA
<213> ORGANISM: P44-19
<220> FEATURE:
<221> NAME/KEY: CDS
<222> LOCATION: (1)..(492)

<400> SEQUENCE: 11 gct aag gag tta gct tat gat gtt gtt act gga cag act gat aac ctt      48
Ala Lys Glu Leu Ala Tyr Asp Val Val Thr Gly Gln Thr Asp Asn Leu
1               5                   10                  15 gct gct gct ctt gcc aaa acc tca ggt aag gac atc gtt cag ttt gct      96
Ala Ala Ala Leu Ala Lys Thr Ser Gly Lys Asp Ile Val Gln Phe Ala
                20                  25                  30 aag gcg gtg gag ata tcc tcc ccc acc att gat ggg aag att tgt aag     144
Lys Ala Val Glu Ile Ser Ser Pro Thr Ile Asp Gly Lys Ile Cys Lys
            35                  40                  45 ata aat aca gga agt aat aaa tac ggc act gga aca aat tct gga gaa     192
Ile Asn Thr Gly Ser Asn Lys Tyr Gly Thr Gly Thr Asn Ser Gly Glu
        50                  55                  60 ctc act tgt gga gtt ggc cac gcg agc gga tct cta gga gcg gcg aac     240
Leu Thr Cys Gly Val Gly His Ala Ser Gly Ser Leu Gly Ala Ala Asn
65                  70                  75                  80 gga gcc ttt aag gat ttt cga cag cat gtg tta gaa gtt gaa agt cat     288
Gly Ala Phe Lys Asp Phe Arg Gln His Val Leu Glu Val Glu Ser His
                85                  90                  95 aaa cat tgg cct act acg cag ggt tct agt gat aaa ggt agt aat aac     336
Lys His Trp Pro Thr Thr Gln Gly Ser Ser Asp Lys Gly Ser Asn Asn
            100                 105                 110 gca aca aag gta gcc gga gaa cta aca aag ctc acc aca gaa gaa aaa     384
Ala Thr Lys Val Ala Gly Glu Leu Thr Lys Leu Thr Thr Glu Glu Lys
        115                 120                 125 acc ata gta gca ggg tta cta gct aaa act att gaa ggg gga gag gtt     432
Thr Ile Val Ala Gly Leu Leu Ala Lys Thr Ile Glu Gly Gly Glu Val
130                 135                 140 gtt gaa atc agg gct gtc tct tct act tct gtg atg gtt aat gct tgt     480
Val Glu Ile Arg Ala Val Ser Ser Thr Ser Val Met Val Asn Ala Cys
145                 150                 155                 160 tat gat ctt ctt                                                      492
Tyr Asp Leu Leu
```

<210> SEQ ID NO 12
<211> LENGTH: 164
<212> TYPE: PRT
<213> ORGANISM: P44-19

<400> SEQUENCE: 12

```
Ala Lys Glu Leu Ala Tyr Asp Val Val Thr Gly Gln Thr Asp Asn Leu
 1               5                  10                  15

Ala Ala Ala Leu Ala Lys Thr Ser Gly Lys Asp Ile Val Gln Phe Ala
            20                  25                  30

Lys Ala Val Glu Ile Ser Ser Pro Thr Ile Asp Gly Lys Ile Cys Lys
        35                  40                  45

Ile Asn Thr Gly Ser Asn Lys Tyr Gly Thr Gly Thr Asn Ser Gly Glu
    50                  55                  60

Leu Thr Cys Gly Val Gly His Ala Ser Gly Ser Leu Gly Ala Ala Asn
65                  70                  75                  80

Gly Ala Phe Lys Asp Phe Arg Gln His Val Leu Glu Val Glu Ser His
                85                  90                  95

Lys His Trp Pro Thr Thr Gln Gly Ser Ser Asp Lys Gly Ser Asn Asn
            100                 105                 110

Ala Thr Lys Val Ala Gly Glu Leu Thr Lys Leu Thr Thr Glu Glu Lys
        115                 120                 125

Thr Ile Val Ala Gly Leu Leu Ala Lys Thr Ile Glu Gly Gly Glu Val
    130                 135                 140

Val Glu Ile Arg Ala Val Ser Ser Thr Ser Val Met Val Asn Ala Cys
145                 150                 155                 160

Tyr Asp Leu Leu
```

<210> SEQ ID NO 13
<211> LENGTH: 11
<212> TYPE: PRT
<213> ORGANISM: Hypervariable region of P44 protein

<400> SEQUENCE: 13

```
Asn Ala Asn Ala Met Ala Lys Asp Leu Val Lys
 1               5                  10
```

<210> SEQ ID NO 14
<211> LENGTH: 11
<212> TYPE: PRT
<213> ORGANISM: Hypervariable region of P44-2 protein

<400> SEQUENCE: 14

```
Asn Ala Lys Ala Val Ala Thr Asp Leu Val Gln
 1               5                  10
```

<210> SEQ ID NO 15
<211> LENGTH: 11
<212> TYPE: PRT
<213> ORGANISM: Hypervariable region of P44-12 protein

<400> SEQUENCE: 15

```
Asn Ala Glu Ala Val Ala Lys Asp Leu Val Gln
 1               5                  10
```

<210> SEQ ID NO 16
<211> LENGTH: 11
<212> TYPE: PRT
<213> ORGANISM: Hypervariable region of P44-15 protein -continued

```
<400> SEQUENCE: 16

Asn Ala Lys Ala Val Ala Lys Asp Leu Val Gln
1               5                   10

<210> SEQ ID NO 17
<211> LENGTH: 11
<212> TYPE: PRT
<213> ORGANISM: Hypervariable region of P44-18 protein

<400> SEQUENCE: 17

Asn Ala Lys Ala Val Ala Gly Asp Leu Thr Lys
1               5                   10

<210> SEQ ID NO 18
<211> LENGTH: 11
<212> TYPE: PRT
<213> ORGANISM: Hypervariable region of P44-19 protein

<400> SEQUENCE: 18

Asn Ala Thr Lys Val Ala Gly Glu Leu Thr Lys
1               5                   10

<210> SEQ ID NO 19
<211> LENGTH: 15
<212> TYPE: PRT
<213> ORGANISM: Synthetic oligopeptide of P44 protein

<400> SEQUENCE: 19

Leu Ser Asn Gly Ser Ala Glu Ala Ala His Lys Tyr Leu Ser Lys
1               5                   10                  15

<210> SEQ ID NO 20
<211> LENGTH: 15
<212> TYPE: PRT
<213> ORGANISM: Synthetic oligopeptide of P44-2 protein

<400> SEQUENCE: 20

Gly His Ser Ser Gly Val Thr Gln Asn Pro Lys Leu Phe Ser Thr
1               5                   10                  15

<210> SEQ ID NO 21
<211> LENGTH: 15
<212> TYPE: PRT
<213> ORGANISM: Synthetic oligopeptide of P44-12 protein

<400> SEQUENCE: 21

Gly Lys Lys Ser Gly Asp Asn Gly Ser Leu Ala Asp Tyr Thr Asp
1               5                   10                  15

<210> SEQ ID NO 22
<211> LENGTH: 16
<212> TYPE: PRT
<213> ORGANISM: Synthetic oligopeptide of P44-15 protein

<400> SEQUENCE: 22

Pro Leu Tyr Ser Asp Glu Thr His Thr Lys Gly Ala Ser Glu Gly Arg
1               5                   10                  15

<210> SEQ ID NO 23
<211> LENGTH: 15
<212> TYPE: PRT
<213> ORGANISM: Synthetic oligopeptide of P44-18 protein

<400> SEQUENCE: 23
```

```
Lys Asn Gln Lys Ser Ser Asp Thr Asp Thr Gly Val Glu Lys Ala
 1               5                  10                  15
```

<210> SEQ ID NO 24
<211> LENGTH: 16
<212> TYPE: PRT
<213> ORGANISM: Synthetic oligopeptide of P44-19 protein

<400> SEQUENCE: 24

```
Thr Gly Ser Asn Lys Tyr Gly Thr Gly Thr Asn Ser Gly Glu Leu Thr
 1               5                  10                  15
```

<210> SEQ ID NO 25
<211> LENGTH: 21
<212> TYPE: DNA
<213> ORGANISM: Primer P3708

<400> SEQUENCE: 25
gctaaggagt tagcttatga t                                      21

<210> SEQ ID NO 26
<211> LENGTH: 20
<212> TYPE: DNA
<213> ORGANISM: Primer P4257

<400> SEQUENCE: 26
aagaagatca taacaagcat                                         20

<210> SEQ ID NO 27
<211> LENGTH: 20
<212> TYPE: DNA
<213> ORGANISM: Primer 2hvf

<400> SEQUENCE: 27
tactggtagc catgctgacc                                         20

<210> SEQ ID NO 28
<211> LENGTH: 21
<212> TYPE: DNA
<213> ORGANISM: Primer 2hvr

<400> SEQUENCE: 28
aatcacccgt cttcagtgat g                                      21

<210> SEQ ID NO 29
<211> LENGTH: 21
<212> TYPE: DNA
<213> ORGANISM: Primer 18hvf

<400> SEQUENCE: 29
ggagatttct aattccggta t                                      21

<210> SEQ ID NO 30
<211> LENGTH: 21
<212> TYPE: DNA
<213> ORGANISM: Primer 18hvf

<400> SEQUENCE: 30
agtcattatt cgatttagac g                                      21

<210> SEQ ID NO 31
<211> LENGTH: 21
<212> TYPE: DNA
<213> ORGANISM: Primer 12hvf

<400> SEQUENCE: 31
tgataagaag gtttgtgatg g                                              21

<210> SEQ ID NO 32
<211> LENGTH: 21
<212> TYPE: DNA
<213> ORGANISM: Primer 12 hvr

<400> SEQUENCE: 32
agagcacatt aacgttgtca c                                              21

<210> SEQ ID NO 33
<211> LENGTH: 21
<212> TYPE: DNA
<213> ORGANISM: Primer 15hvf

<400> SEQUENCE: 33
gaaggtttgt aagacgaagg c                                              21

<210> SEQ ID NO 34
<211> LENGTH: 21
<212> TYPE: DNA
<213> ORGANISM: Primer 15hvr

<400> SEQUENCE: 34
agttcgtgac aggttttgga g                                              21

<210> SEQ ID NO 35
<211> LENGTH: 22
<212> TYPE: DNA
<213> ORGANISM: Primer 19hvf

<400> SEQUENCE: 35
cattgatggg aagatttgta ag                                             22

<210> SEQ ID NO 36
<211> LENGTH: 21
<212> TYPE: DNA
<213> ORGANISM: Primer 19hvr

<400> SEQUENCE: 36
aggtgagctt tgttagttct c                                              21

<210> SEQ ID NO 37
<211> LENGTH: 21
<212> TYPE: DNA
<213> ORGANISM: Primer 44hvf

<400> SEQUENCE: 37
gaaggtttgt agtggaaagc a                                              21

<210> SEQ ID NO 38
<211> LENGTH: 21
<212> TYPE: DNA
<213> ORGANISM: Primer 44hvr

<400> SEQUENCE: 38
atgctccaac tacaatgcta t                                              21

<210> SEQ ID NO 39
<211> LENGTH: 21
<212> TYPE: DNA

-continued

```
<213> ORGANISM: Primer pnf12

<400> SEQUENCE: 39
caagtttgac tggaacactc c                                        21

<210> SEQ ID NO 40
<211> LENGTH: 20
<212> TYPE: DNA
<213> ORGANISM: Primer pnr12

<400> SEQUENCE: 40
aacaatatct ttaccagagg                                          20

<210> SEQ ID NO 41
<211> LENGTH: 21
<212> TYPE: DNA
<213> ORGANISM: Primer pcf12

<400> SEQUENCE: 41
ctaaagacct agtacaggag c                                        21

<210> SEQ ID NO 42
<211> LENGTH: 21
<212> TYPE: DNA
<213> ORGANISM: Primer pcr12

<400> SEQUENCE: 42
gagagagctg ataactcaac c                                        21

<210> SEQ ID NO 43
<211> LENGTH: 23
<212> TYPE: DNA
<213> ORGANISM: NH2-terminal of HGE agent of P44

<400> SEQUENCE: 43
cgccatggct gggagtgatg tca                                      23

<210> SEQ ID NO 44
<211> LENGTH: 27
<212> TYPE: DNA
<213> ORGANISM: oligonucleotide primers of P44

<400> SEQUENCE: 44
gcgaattcta cgcactacca ttactca                                  27
```